(12) United States Patent
Rieder et al.

(10) Patent No.: US 10,371,553 B2
(45) Date of Patent: Aug. 6, 2019

(54) TRANSDUCER APPARATUS AS WELL AS MEASURING SYSTEM FORMED THEREWITH

(71) Applicant: Endress + Hauser Flowtec AG, Reinach (CH)

(72) Inventors: Alfred Rieder, Landshut (DE); Hao Zhu, Freising (DE); Ennio Bitto, Aesch (CH); Gerhard Eckert, Grenzach-Wyhlen (DE); Josef Hubensteiner, Freising (DE); Michael Wiesmann, Freising (DE); Yaoing Lin, Freising (DE)

(73) Assignee: ENDRESS + HAUSER FLOWTEC AG, Reinach (CH)

( * ) Notice: Subject to any disclaimer, the term of this patent is extended or adjusted under 35 U.S.C. 154(b) by 262 days.

(21) Appl. No.: 15/125,315

(22) PCT Filed: Feb. 23, 2015

(86) PCT No.: PCT/EP2015/053677
§ 371 (c)(1),
(2) Date: Sep. 12, 2016

(87) PCT Pub. No.: WO2015/135738
PCT Pub. Date: Sep. 17, 2015

(65) Prior Publication Data
US 2017/0074701 A1    Mar. 16, 2017

(30) Foreign Application Priority Data
Mar. 13, 2014 (DE) .................. 10 2014 103 427

(51) Int. Cl.
*G01F 1/84*    (2006.01)
*G01N 11/16*   (2006.01)
(Continued)

(52) U.S. Cl.
CPC ............ *G01F 1/8413* (2013.01); *G01F 1/849* (2013.01); *G01F 15/02* (2013.01); *G01F 15/14* (2013.01);
(Continued)

(58) Field of Classification Search
CPC ........ G01F 1/8413; G01F 1/849; G01F 15/02; G01F 15/14; G01N 9/002; G01N 11/16
See application file for complete search history.

(56) References Cited

U.S. PATENT DOCUMENTS 7,216,550 B2    5/2007  Lesjak
7,734,431 B2 *  6/2010  Nitschke ............... G01F 1/8436
                                                        702/51
(Continued)

FOREIGN PATENT DOCUMENTS

DE    102005053096 A1    5/2007
DE    102010040598 A1    3/2012
(Continued)

OTHER PUBLICATIONS

German Search Report, German Patent Office, Munich, DE, dated Sep. 24, 2014.
(Continued)

*Primary Examiner* — David Z Huang
(74) *Attorney, Agent, or Firm* — Bacon & Thomas, PLLC

(57) ABSTRACT transducer apparatus comprises a transducer housing, a tube, a temperature sensor as well as a temperature sensor. The tube is arranged within a cavity of the transducer housing, in such a manner that an intermediate space is formed between a wall of the transducer housing facing the cavity inner surface and an outer surface of a wall of the tube facing the cavity. Furthermore, the tube is adapted to guide a fluid in its lumen, in such a manner that an inner surface of the wall of the tube facing the lumen is contacted by fluid guided in the
(Continued)

lumen. Each of the temperature sensors is formed by means of a temperature detector arranged within the intermediate space as well as by means of a coupling body coupling the respective temperature detector thermally conductively with the wall of the tube and is additionally adapted to register a particular measurement location temperature, and to transduce such into a corresponding temperature measurement signal, namely an electrical measurement signal representing the particular measurement location temperature.

35 Claims, 10 Drawing Sheets

(51) Int. Cl.
    *G01F 15/02*     (2006.01)
    *G01F 15/14*     (2006.01)
    *G01N 9/00*     (2006.01)
    *G01N 11/00*     (2006.01)

(52) U.S. Cl.
    CPC ............. *G01N 9/002* (2013.01); *G01N 11/16* (2013.01); *G01N 2009/006* (2013.01); *G01N 2011/0013* (2013.01)

(56) References Cited

U.S. PATENT DOCUMENTS

| | | |
|---|---|---|
| 8,857,270 B2 | 10/2014 | Zhu |
| 9,134,165 B2 | 9/2015 | Kirst |
| 2017/0074701 A1 | 3/2017 | Rieder |

FOREIGN PATENT DOCUMENTS

| | | |
|---|---|---|
| DE | 102011080415 A1 | 2/2013 |
| DE | 102014103427 A1 | 9/2015 |
| EP | 1530030 A2 | 5/2005 |
| WO | 2008064459 A1 | 6/2008 |

OTHER PUBLICATIONS

International Search Report, EPO, The Netherlands, dated Mar. 28, 2015.
English Translation of the International Preliminary Report on Patentability, WIPO, Geneva, CH, dated Sep. 22, 206.

* cited by examiner

TRANSDUCER APPARATUS AS WELL AS MEASURING SYSTEM FORMED THEREWITH

TECHNICAL FIELD

The invention relates to a transducer apparatus suitable for measuring a target temperature of the transducer apparatus, equally as well, a time variable target temperature, especially a temperature of a fluid guided in a lumen of a tube, and/or a temperature of a wall of such a tube contacted by the fluid. Furthermore, the invention relates also to a measuring system formed by means of such a transducer apparatus.

BACKGROUND DISCUSSION

Transducer apparatuses of the type being discussed comprise a transducer housing having a cavity encased by a wall, typically a metal wall, as well as a tube having a lumen surrounded by a wall, typically likewise a metal wall, and arranged within the cavity of the transducer housing, in such a manner that, between an inner surface of the wall of the transducer housing facing the cavity and an outer surface of the wall of the tube, namely an outer, surface of the wall of the tube facing the cavity, an intermediate space is formed, most often an intermediate space filled with air or an inert gas. The at least one tube is, especially, adapted to guide in its lumen a fluid flowing, at least at times, for example, a fluid in the form of a gas, a liquid or a flowable dispersion, in such a manner that an inner surface of the wall of the tube facing the lumen is contacted by fluid guided in the lumen to form a first interface of a first type, namely an interface between a fluid and a solid phase. In order to measure a target temperature, namely a temperature of the respective transducer apparatus, equally as well a time variable temperature, at a predefined measuring, respectively reference, point within the respective transducer apparatus, such transducer apparatuses comprise, furthermore, at least two temperature sensors formed, in each case, by means of a temperature detector arranged within the intermediate space and, consequently, during operation not contacted by the fluid in the lumen of the at least one tube, wherein at least one of the temperature sensors has a coupling body connecting its temperature detector thermally conductively with the wall, for example, a coupling body formed by means of thermally conductive adhesive. Each of such temperature detectors can be, for example, a platinum measuring resistor, a thermistor or a thermocouple or, however, electrical circuits formed by means of a plurality of such temperature sensitive, electrical, respectively electronic, components. Each of the at least two temperature sensors is adapted to transduce a measurement location temperature corresponding to a temperature at a temperature measurement location formed by means of the respective temperature detector, in each case, into a corresponding temperature measurement signal, namely an electrical measurement signal representing the particular measurement location temperature, for example, an electrical measurement signal having an electrical signal voltage dependent on the measurement location temperature and/or an electrical signal current dependent on the measurement location temperature. Target temperature in the case of such transducer apparatuses can be, for example, a measured fluid temperature, namely a temperature of the fluid guided during operation of the transducer apparatus in the lumen of the at least one tube, and/or a tube temperature, namely a temperature of the wall of the tube contacted by the fluid respectively located in the lumen.

The transducer apparatus can, furthermore, be connected to a measuring and operating electronics, formed, for example, by means of at least one microprocessor, to form a measuring system for measuring at least one measured variable, for example, namely the temperature of the measured fluid or also a density and/or a viscosity of the fluid guided in the at least one tube of the respective transducer apparatus. The measuring and operating electronics can, in turn, be adapted, with application of the at least two temperature measurement signals generated by means of the transducer apparatus, to generate a measured value, which represents the at least one measured variable. In the case of such measuring systems, the measuring and operating electronics is typically accommodated within at least one, comparatively robust, especially impact-, pressure-, and/or weather resistant, electronics housing. The electronics housing can, for example, be arranged removed from the transducer system and connected with such only via a flexible cable; it can, however, also be directly arranged on the transducer housing, respectively affixed thereto. Further examples of transducer apparatuses of the type being discussed, respectively measuring systems formed therewith, are shown in, among others, European Application, EP-A 919 793, US-A 2004/0187599, US-A 2008/0127745, US-A 2011/0113896, U.S. Pat. Nos. 4,768,384, 5,602,346, 6,047, 457, 7,040,179, 7,549,319, Published International Applications WO-A 01/02816, WO-A 2009/051588, WO-A 2009/134268, WO-A 2012/018323, WO-A 2012/033504, WO-A 2012/067608 or WO-A 2012/115639.

In the case of measuring systems of the above indicated type used in industrial measuring and automation technology, the particular measuring and operating electronics is usually electrically connected via corresponding electrical lines also to a superordinated electronic data processing system arranged most often spatially removed from the respective measuring system and most often also spatially distributed, to which the measured values produced by the respective measuring system and correspondingly carried by means of at least one of these measured value signals are forwarded near in time, for example, also in real time. Measuring systems of the type being discussed are additionally usually connected with one another and/or to corresponding electronic process controllers by means of a data transmission network provided within the superordinated data processing system, for example, to programmable logic controllers (PLC) installed on-site or to process control computers installed in a remote control room, where the measured values produced by means of the respective measuring system and digitized in suitable manner and correspondingly encoded are forwarded. By means of such process control computers, the transmitted measured values can be further processed and visualized as corresponding measurement results e.g. on monitors and/or converted into control signals for other field devices, such as e.g. magnet-operated valves, electric motors, etc., embodied as actuating devices. Since modern measuring arrangements can also be monitored and, in given cases, controlled and/or configured most often directly from such control computers, in corresponding manner, operating data intended for the measuring system are equally sent via the aforementioned data transmission networks, which are most often hybrid as regards the transmission physics and/or the transmission logic. Accordingly, the data processing system usually also serves to condition, for example, suitably to digitize and, in given cases, to convert into a corresponding telegram, the measured value signal delivered by the measuring system, corresponding to the requirements of downstream data transmission networks, and/or to evaluate such on-site. For such purpose, there are provided in such data processing systems, electrically coupled with the respective connecting lines, evaluating circuits, which pre- and/or further process as well as, in case required, suitably convert the measured values received by the respective measuring system. Serving for data transmission in such industrial data processing systems at least sectionally, especially serially, are fieldbusses, such as e.g. FOUNDATION FIELDBUS, RACKBUS-RS 485, PROFIBUS, etc., fieldbusses, or, for example, also networks based on the ETHERNET standards, as well as the corresponding, most often comprehensively standardized, transmission protocols. Alternatively or supplementally, in the case of modern measuring systems of the type being discussed, measured values can also be transmitted wirelessly per radio to the particular data processing system. Besides the evaluating circuits required for processing and converting the measured values delivered from the respectively connected measuring system, such superordinated data processing systems have most often also electrical supply circuits serving for supplying the connected measuring systems with electrical energy and providing a corresponding supply voltage, in given cases, fed directly by the connected fieldbus, for the respective electronics and the thereto connected electrical lines as well as for driving electrical currents flowing through the respective electronics. A supply circuit can, in such case, be associated with, for example, exactly one measuring system, respectively a corresponding electronics, and be accommodated together with the evaluating circuit associated with the respective measuring system, for example, combined in a corresponding fieldbus adapter, in a shared electronics housing, e.g. formed as a top hat rail module. It is, however, also quite usual to accommodate supply circuits and evaluating circuits in separate electronics housings, in given cases, spatially remotely from one another, and to connect them correspondingly together via external cables.

Transducer apparatuses of the type being discussed are applied not least of all also in vibronic measuring systems serving for ascertaining measured variables, for example, a mass flow rate, a density or a viscosity, of fluids guided in a process line, for example, a pipeline, respectively they can be an integral component of such a measuring system. Construction and operation of such vibronic measuring systems formed by means of such a transducer apparatus, for example, also measuring systems in the form of Coriolis, mass flow, measuring devices or also Coriolis, mass flow, measuring systems, are known, per se, to those skilled in the art and are described at length and in detail, for example, also in the above mentioned EP-A 919 793, US-A 2004/0187599, US-A 2008/0127745, US-A 2011/0113896, U.S. Pat. Nos. 4,768,384, 5,602,346, 7,040,179, 7,549,319, WO-A 01/02816, WO-A 2009/051588, WO-A 2009/134268, WO-A 2012/018323, WO-A 2012/033504, WO-A 2012/067608, WO-A 2012/115639, or, for example, also in US-A 2001/0037690, US-A 2011/0265580, US-A 2011/0146416, US-A 2011/0113896, US-A 2010/0242623, and Published International Applications, WO-A 2013/092104, WO-A 01/29519, WO-A 98/02725, WO-A 94/21999 or WO-A 88/02853. In the case of such vibronic measuring systems, the at least one tube of the respective transducer apparatus is, especially, also adapted, for the purpose of measuring the at least one measured variable, during operation, at least at times, to be caused to vibrate while filled with fluid to be measured, respectively flowed through by the fluid to be measured. Typically, the at least one tube is actively excited by means of at least one electromechanical oscillation exciter of the transducer apparatus acting thereon, for example, an oscillation exciter formed by means of a permanent magnet affixed to the at least one tube and by means of an exciter coil interacting therewith, to execute wanted oscillations, namely mechanical oscillations about a static resting position associated with the respective tube, especially also such mechanical oscillations, which are suitable to induce in the flowing fluid Coriolis forces dependent on a mass flow rate, m, and/or which are suitable to induce in the flowing fluid frictional forces dependent on a viscosity, η, and/or which are suitable to induce in the flowing fluid inertial forces dependent on a density, ρ. For registering mechanical oscillations of the at least one tube, not least of all also its wanted oscillations, the transducer apparatuses used in such vibronic measuring systems have, furthermore, in each case, at least one oscillation sensor, for example, an electrodynamic, oscillation sensor, which is adapted to produce at least one oscillatory signal, namely an electrical measurement signal representing oscillatory movements of the at least one tube, for example, with an electrical signal voltage dependent on a velocity of the oscillatory movements of the at least one tube. The measuring and operating electronics of such vibronic measuring systems is—not least of all for the case, in which the at least one measured value represents a density or a viscosity of the fluid guided in the at least one tube —, further adapted to generate the at least one measured value using both the at least two temperature measurement signals generated by means of the transducer apparatus as well as also the at least one oscillation signal, for example, in such a manner that the measuring and operating electronics ascertains the at least one measured value based on a wanted frequency measured based on the oscillation signal, namely an oscillation frequency of the wanted oscillations dependent on the measured variable to be measured and for this purpose metrologically compensates a possible dependence of the wanted frequency also on an instantaneous, measured fluid temperature, respectively a temperature distribution within the wall of the at least one tube.

In the case of modern measuring systems used in industrial measuring and automation technology, not least of all also in the case of vibronic measuring systems of the above indicated type, the measuring and operating electronics is most often formed by means of one or more microprocessors, in given cases, also implemented as digital signal processors (DSP), in such a manner that the measuring and operating electronics ascertains the respective measured values for the at least one measured variable by numerical processing of digital, sampled values of measurement signals of the respective transducer apparatus, for example, namely digital, sampled values won from the at least two temperature measurement signals, respectively the at least one oscillatory signal, and provided in the form of corresponding digital values. Besides the evaluation of the temperature measurement signals as well as the at least one oscillation signal, the measuring and operating electronics of vibronic measuring systems of the above indicated type serves typically also to generate at least one driver signal, for example, a harmonic and/or clocked, driver signal, for the at least one electromechanical oscillation exciter. The driver signal can be controlled, for example, as regards an electrical current level and/or a voltage level.

As evident, among others, from the above mentioned U.S. Pat. Nos. 4,768,384, 7,040,179, respectively US-A 2008/0127745, a special problem of ascertaining a temperature in transducer apparatuses of the type being discussed, be it a measured fluid temperature or a tube temperature, is that the measurement location temperatures registered by means of the at least two, in given cases, also three or more, temperature sensors correspond, first of all, in each case, actually only to a local temperature at exactly the temperature measurement location formed by means of the respective temperature detector, that, however, conversely, most often actually a local, respectively average temperature at another apparatus reference point, namely a reference point within the transducer apparatus remote from each of the temperature measurement locations, is of interest (target temperature), for example, namely—not least of all for the purpose of ascertaining the measured fluid temperature—a temperature within the lumen of the at least one tube, and/or—not least of all for the purpose of correction of a dependence of the wanted frequency on a spatial temperature distribution within the wall of the at least one tube—actually a spatially averaged tube temperature should serve as a target temperature. A further problem can additionally be that as a result of unavoidable time changes of the measured fluid temperature within the transducer apparatus regularly also dynamic heat equilibration processes can take place, which likewise, not least of all due to the only very limited number of temperature measurement locations, respectively due to their mutual spatial separation, can lead to defective measurement results in measuring systems formed by means of transducer apparatuses of the type being discussed, be it in the case of ascertaining the measured fluid temperature or, for instance, in the case of application of the transducer apparatus in a vibronic measuring system, in the case of which measured variables, such as e.g. the density and/or the viscosity of a fluid guided in the at least one tube or also a mass flow rate of a fluid flowing through the at least one tube, are ascertained based on wanted oscillations of the at least one tube. Moreover, such as also discussed, among others, in the above mentioned WO-A 2009/051588, also an ambient temperature of the transducer, namely a temperature of an atmosphere surrounding the transducer housing, respectively a time change of the ambient temperature, can degrade the accuracy, with which the measured fluid temperature, respectively the tube temperature, can be ascertained by means of such transducer apparatuses.

Further investigations on the part of the inventors have, furthermore, shown that, besides the above indicated influences, surprisingly, however, also a temperature difference, respectively its time change, existing between the measured fluid temperature and the tube ambient temperature, namely a temperature of the fluid volume in the intermediate space formed between the inner surface of the wall of the transducer housing and the outer surface of the wall of the tube, consequently the fluid volume surrounding the tube, can influence the respective temperature measurement signals. Fundamentally, namely each of the temperature sensors is via a respective surface facing the intermediate space thermally coupled—more or less strongly—also to the fluid volume kept in the intermediate space, in such a manner that a heat transfer taking place between the fluid within the lumen of the tube and the fluid volume surrounding the tube regularly leads partially also through the respective temperature sensors. Due to such a heat transfer, respectively, associated therewith, also due to heat transport processes respectively transpiring between each of the temperature sensors and the fluid volume formed in the intermediate space, the respective measurement location temperature is, thus, dependent not only on the tube —, respectively the measured fluid, temperature, but, instead, regularly also mentionably co-determined by the ambient temperature of the tube. Moreover, the inventors could also detect that the above-mentioned thermal coupling can, at times, assume such an extent that, as regards the high accuracy of measurement desired for measuring systems of the type being discussed, not least of all also for vibronic measuring systems, it is actually no longer negligible, respectively that, conversely, an ignoring of the influence of such temperature difference on the respectively registered measurement location temperature, respectively the temperature measurement signal representing such, can lead to quite significant measurement errors, for instance, in such a manner that the measured values for the target temperature ascertained, in each case, by means of the respective measuring system, especially also in the case of time constant target temperature, deviate, at times, by more than 0.5 K from the actual, respectively true, target temperature.

SUMMARY OF THE INVENTION

Taking this into consideration, an object of the invention is so to improve transducer apparatuses of the aforementioned type that even with two temperature sensors arranged, in each case, outside of the lumen of the at least one tube, equally as well within the transducer housing, an (in comparison to conventional transducer apparatuses) more precise ascertaining of a target temperature, for example, namely the measured fluid temperature and/or a tube temperature, reigning at a predetermined, respectively earlier fixed, equally as well removed from each of the at least two temperature sensors, apparatus reference point located within the transducer housing is enabled, respectively that the target temperature, lying not least of all also in a typical working range for transducer apparatuses of the type being discussed, for instance, between −40° C. and +150° C., can be determined with a measuring error of less than 0.2 K; this not least of all also for the case, in which the particular tube temperature, respectively measured fluid temperature and/or the particular transducer—, respectively tube, ambient temperature varies in an unpredictable manner with respect to time, respectively the temperature difference existing between the measured fluid temperature and the tube ambient temperature fluctuates over a broad temperature range.

For achieving the object, the invention resides in a transducer apparatus, which comprises a transducer housing having a cavity encased by a wall, for example, a metal wall, as well as a tube having a lumen surrounded by a wall, for example, a metal wall, wherein the tube is arranged within the cavity of the transducer housing in such a manner that between an inner surface of the wall of the transducer housing facing the cavity and an outer surface of the wall of the tube facing the cavity an intermediate space is formed, and wherein the tube is adapted to guide in its lumen a fluid, especially a fluid flowing at least at times, for example, a gas, a liquid or a flowable dispersion, in such a manner that an inner surface of the wall of the tube facing the lumen is contacted by fluid guided in the lumen in order to form a first interface of a first type, namely an interface between a fluid and a solid phase. The transducer housing and the tube of the transducer apparatus of the invention are additionally adapted to hold a fluid in the intermediate space, for example, a fluid having a specific thermal conductivity of less than 1 W/(m·K), for example, namely air or an inert gas, in order to form a fluid volume surrounding the tube, in such a manner that the outer surface of the wall of the tube facing the intermediate space is contacted by fluid held in the intermediate space, in order to form a second interface of a first type. The transducer apparatus of the invention further comprises a first temperature sensor formed by means of a first temperature detector arranged within the intermediate space and formed, for example, by means of a platinum measuring resistor, a thermistor or a thermocouple, as well as by means of a first coupling body coupling the first temperature detector thermally conductively with the wall of the tube, wherein the first temperature sensor serves for transducing a first measurement location temperature, namely a temperature at a first temperature measurement location formed by means of the first temperature detector, into a first temperature measurement signal, namely a first electrical measurement signal representing the first measurement location temperature, for example, a first electrical measurement signal having an electrical signal voltage dependent on the first measurement location temperature and/or an electrical signal current dependent on the first measurement location temperature, as well as a second temperature sensor formed by means of a second temperature detector spaced from the first temperature detector, arranged within the intermediate space and formed, for example, by means of a platinum measuring resistor, a thermistor or a thermocouple, as well as by means of a second coupling body coupling the second temperature detector thermally conductively with the wall of the tube, wherein the second temperature sensor serves for transducing a second measurement location temperature, namely a temperature at a second temperature measurement location formed by means of the second temperature detector, into a second temperature measurement signal, namely a second electrical measurement signal representing the second measurement location temperature, for example, a second electrical measurement signal having an electrical signal voltage dependent on the second measurement location temperature and/or an electrical signal current dependent on the second measurement location temperature. The first temperature sensor contacts by means of the first coupling body the outer surface of the wall of the tube to form a first interface of a second type, namely an interface between two solid phases, and the second temperature sensor contacts by means of the second coupling body the outer surface of the wall of the tube to form a second interface of a second type, in such a manner that a first thermal resistance opposes a heat flux resulting from a temperature difference reigning between the first interface of a second type and the first temperature measurement location, totally passing through the interface and flowing further to the first temperature measurement location and a second thermal resistance, R2, opposes a heat flux resulting from a temperature difference reigning between the second interface of a second type and the second temperature measurement location, totally passing through the interface and flowing further to the second temperature measurement location. The fluid volume surrounding the tube, in turn, contacts the first temperature sensor (via an outer surface of the temperature sensor facing the intermediate space) to form a third interface of a first type as well as contacts the second temperature sensor (via an outer surface of the temperature sensor facing the intermediate space) to form a fourth interface of a first type, in such a manner that a third thermal resistance, R3, opposes a heat flux resulting from a temperature difference reigning between the third interface of first type and the first temperature measurement location, flowing from the first temperature measurement location totally to the interface, equally as well totally passing through the interface and a fourth thermal resistance, R4, opposes a heat flux resulting from a temperature difference reigning between the fourth interface of a first type and the second temperature measurement location, flowing from the second temperature measurement location totally to the interface, equally as well totally passing through the interface. In the case of the transducer apparatus of the invention, the first thermal resistance, R1, the second thermal resistance, R2, the third thermal resistance, R3, as well as the fourth thermal resistance, R4, are so dimensioned, matched to one another, that, as a whole, a condition is fulfilled.

$$0.005 < \frac{1+\frac{R4}{R2}}{1+\frac{R3}{R1}} < 1$$

Moreover, the invention resides also in a measuring system for measuring at least one measured variable, for example, a temperature, a density and/or a viscosity, of a flowing fluid, for example, a gas, a liquid or a flowable dispersion, which measuring system comprises a measuring and operating electronics, for example, one formed by means of a microprocessor, and, for guiding the fluid, an above-referenced transducer apparatus of the invention.

In a first embodiment of the transducer apparatus of the invention, it is provided that the first thermal resistance, R1, is less than 1000 K/W, and the thermal resistance, R2, is less than 1000 K/W.

In a second embodiment of the transducer apparatus of the invention, it is provided that the first thermal resistance, R1, is less than 30 K/W, especially less than 25 K/W.

In a third embodiment of the transducer apparatus of the invention, it is provided that the third thermal resistance, R3, and the fourth thermal resistance, R4, fulfill a condition R3=R4.

In a fourth embodiment of the transducer apparatus of the invention, it is provided that the first thermal resistance, R1, the second thermal resistance, R2, the third thermal resistance, R3, as well as the fourth thermal resistance, R4 fulfill a condition $$\frac{1+\frac{R4}{R2}}{1+\frac{R3}{R1}} < 0.9.$$

In a fifth embodiment of the transducer apparatus of the invention, it is provided that the first thermal resistance, R1, the second thermal resistance, R2, the third thermal resistance, R3, as well as the fourth thermal resistance, R4 fulfill a condition $$\frac{1+\frac{R4}{R2}}{1+\frac{R3}{R1}} > 0.01.$$

In a sixth embodiment of the transducer apparatus of the invention, it is provided that the first coupling body is composed at least partially, for example, also predominantly or completely, of a material, for instance, a thermally conductive adhesive, of which a specific thermal conductivity, $\lambda 712$, is greater than a specific thermal conductivity, $\lambda F$, of the fluid in the intermediate space and/or greater than 1 W/(m·K), and of which a specific heat capacity, cp712, is less than a specific heat capacity, cpF, of the fluid in the intermediate space and/or less than 2000 J/(kg·K), for example, also in such a manner that a ratio, λ712/λF, of the specific thermal conductivity, λ712, of the material to the specific thermal conductivity, λF, of the fluid in the intermediate space is greater than 2, and/or that a ratio, cp712/cpF, of the specific heat capacity, cp712, of the material to the specific heat capacity, cpF, of the fluid in the intermediate space is less than 1.5. Developing these embodiments of the invention further, it is, additionally, provided that the second coupling body is composed at least partially, for example, also predominantly or completely, of a material, for instance, a metal, of which material a specific thermal conductivity, λ2, is greater than the specific thermal conductivity, λ1, of the material of the first coupling body and/or greater than 10 W/(m·K), and/or of which material a specific heat capacity, cp2, is less than the specific heat capacity, cp1, of the material of the first coupling body and/or less than 1000 J/(kg·K).

In a seventh embodiment of the transducer apparatus of the invention, it is provided that the third thermal resistance, R3, is greater than 500 K/W, especially greater than 5000 K/W.

In an eighth embodiment of the transducer apparatus of the invention, it is provided that the third thermal resistance, R3, is less than 20000 K/W, especially less than 10000 K/W.

In a ninth embodiment of the transducer apparatus of the invention, it is provided that the fourth thermal resistance, R4, is greater than 500 K/W, especially greater than 5000 K/W.

In a tenth embodiment of the transducer apparatus of the invention, it is provided that the fourth thermal resistance, R4, is less than 20000 K/W, especially less than 10000 K/W.

In an 11$^{th}$ embodiment of the transducer apparatus of the invention, it is provided that the first temperature sensor is formed by means of a third coupling body coupling the first temperature detector thermally with the fluid volume formed in the intermediate space, which third coupling body contacts the fluid volume to form the third interface of a first type. The coupling body can be formed, for example, by means of a synthetic material applied on the first temperature detector, by means of a textile band or tape applied on the first temperature detector, respectively by means of sheet metal applied on the first temperature detector. Developing this embodiment of the invention further, it is, additionally, provided that the second temperature sensor is formed by means of a fourth coupling body coupling the second temperature detector thermally with the fluid volume formed in the intermediate space, for example, a fourth coupling body constructed equally to the third coupling body, wherein the fourth coupling body contacts the fluid volume to form the fourth interface of first type. Also, the fourth coupling body can be formed, for example, by means of a synthetic material applied on the first temperature detector, by means of a textile band or tape applied on the first temperature detector, respectively by means of sheet metal applied on the first temperature detector.

In a twelfth embodiment of the transducer apparatus of the invention, it is provided that the first coupling body has a heat capacity, C1, which is less than 200 J/K, especially less than 100 J/K, and that the second coupling body has a heat capacity, C2, which is less than 200 J/K, especially less than 100 J/K, for example, in such a manner that the heat capacity, C1, of the first coupling body and the second heat capacity, C2, of the second coupling body fulfill a condition $$\frac{1}{10} < \frac{C1}{C2} < 1.$$

Developing this embodiment of the invention further, it is, additionally, provided that the heat capacity, C1, of the first coupling body and the second heat capacity, C2, of the second coupling body fulfill a condition $$\frac{1}{1000} < \frac{C1}{C2} < 1,$$

especially also a condition $$0.01 < \frac{C1}{C2} < 0.9.$$

In a 13$^{th}$ embodiment of the transducer apparatus of the invention, it is provided that the wall of the tube has a wall thickness, which amounts to more than 0.5 mm and/or less than 10 mm.

In a 14th embodiment of the transducer apparatus of the invention, it is provided that the tube has an inner diameter, which amounts to more than 0.5 mm and/or less than 200 mm.

In a 15$^{th}$ embodiment of the transducer apparatus of the invention, the tube is so dimensioned that it has an inner diameter to wall thickness ratio, defined as a ratio of an inner diameter of the tube to a wall thickness of the wall of the tube, which amounts to less than 25:1 and/or more than 5:1.

In a 16$^{th}$ embodiment of the transducer apparatus of the invention, it is provided that the first temperature sensor is connected with the outer surface of the wall of the tube, for example, by means of a thermally conductive adhesive, thus, for example, adhesively, to form the first coupling body by the bonding of materials.

In a 17$^{th}$ embodiment of the transducer apparatus of the invention, it is provided that the first coupling body is formed, for example, also completely, by means of a synthetic material, such as e.g. an epoxide resin or a silicone, located between the wall of the tube and the first temperature detector, for example, a synthetic material contacting both the outer surface of the wall as well as also the first temperature detector and/or containing metal oxide particles. Developing this embodiment of the invention further, it is, additionally, provided that the synthetic material is, for example, a 1-component or 2-component, silicone rubber, such as e.g. DELO-GUM® 3699, of DELO Industrial Adhesives GmbH & Co KGaA, 86949 Windach, Del.

In an 18$^{th}$ embodiment of the transducer apparatus of the invention, it is provided that the second coupling body is formed by means of a disk located between the wall of the tube and the second temperature detector and composed of a metal, respectively an alloy, especially a steel, e.g. one connected with the wall of the tube by the bonding of materials and/or an annular disk, i.e. a washer, and/or one gripping around the tube. Developing this embodiment of the invention further, it is, additionally, provided that the disk has a passageway, especially a circular passageway, having an inner surface facing the outer surface of the wall of the tube.

In a 19$^{th}$ embodiment of the transducer apparatus of the invention, it is provided that the first temperature sensor and the second temperature sensor are spaced azimuthally from one another with reference to a longitudinal axis of the tube.

In a 20th embodiment of the transducer apparatus of the invention, it is provided that the first temperature sensor and the second temperature sensor are spaced axially with reference to a longitudinal axis of the tube, for example, in such a manner that the tube has no imaginary, circular, peripheral line lying in the outer surface, along which line both the first temperature sensor as well as also the second temperature sensor are positioned.

In a 21st embodiment of the transducer apparatus of the invention, it is provided that the tube is at least sectionally, for example, also predominantly or completely, straight, for example, circularly cylindrically straight.

In a 22nd embodiment of the transducer apparatus of the invention, it is provided that the tube is at least sectionally curved, for example, with a circular arc shape.

In a 23rd embodiment of the transducer apparatus of the invention, it is provided that the wall of the tube is at least partially, for example, predominantly or completely, composed of a material, for example, a metal or an alloy, of which a specific thermal conductivity, $\lambda 10$, is greater than 10 W/(m·K), and of which a specific heat capacity, $cp1$, is less than 1000 J/(kg·K).

In a 24th embodiment of the transducer apparatus of the invention, it is provided that the wall of the tube is composed of a metal, respectively an alloy, especially of steel, titanium, zirconium, tantalum.

In a 25th embodiment of the transducer apparatus of the invention, the tube is adapted to execute mechanical oscillations about an associated static resting position.

In a 26th embodiment of the transducer apparatus of the invention, the tube is further adapted to be flowed through by the fluid and during that to be caused to vibrate, for example, also in such a manner that the tube executes mechanical oscillations about a static resting position associated therewith, which are suitable to induce in the flowing fluid Coriolis forces dependent on a mass flow rate, and/or that the tube executes mechanical oscillations about a static resting position associated therewith, which are suitable to induce in the fluid frictional forces dependent on a viscosity of the fluid, and/or that the tube executes mechanical oscillations about a static resting position associated therewith, which are suitable to induce in the fluid inertial forces dependent on a density of the fluid.

In a further development of the transducer apparatus of the invention, such further comprises an oscillation exciter for exciting and maintaining mechanical oscillations of the at least one tube about an associated static resting position, as well as an oscillation sensor for registering mechanical oscillations of the at least one tube.

In a first embodiment of the measuring system of the invention, the transducer apparatus further comprises an oscillation exciter for exciting and maintaining mechanical oscillations of the at least one tube about an associated static resting position, as well as an oscillation sensor for registering mechanical oscillations of the at least one tube, and the measuring and operating electronics is additionally adapted to generate an exciter signal driving the oscillation exciter for exciting mechanical oscillations of the tube. Developing this embodiment of the invention further, the oscillation exciter is, additionally, adapted by means of the exciter signal to excite, respectively to maintain, mechanical oscillations of the tube. Furthermore, the oscillation sensor is adapted to deliver an oscillatory signal representing oscillations of the at least one tube, and the measuring and operating electronics is adapted, using both the first temperature measurement signal as well as also the second temperature measurement signal as well as the oscillation signal, to generate a density measured value, namely a measured value representing a density of the fluid.

In a second embodiment of the measuring system of the invention, the measuring and operating electronics is adapted, using both the first temperature measurement signal generated by means of the transducer apparatus as well as also the second temperature measurement signal generated by means of the transducer apparatus, to generate a measured value, which represents the at least one measured variable, x.

In a third embodiment of the measuring system of the invention, the measuring and operating electronics is adapted, using both the first temperature measurement signal as well as also the second temperature measurement signal, to generate at least one temperature measured value representing a target temperature, namely a temperature at an apparatus reference point predetermined for the measuring system and fixed within the transducer apparatus, for example, an apparatus reference point removed both from the first temperature sensor as well as also from the second temperature sensor and/or located within the tube. Developing this embodiment of the invention further, it is, additionally, provided that the apparatus reference point (poi) is located within the transducer apparatus, for example, namely in the wall of the tube or in the lumen of the tube, for instance, also in such a manner that the temperature measured value represents a tube temperature, namely a temperature assumed by the wall of the tube, respectively in such a manner that the temperature measured value represents a measured fluid temperature, namely a temperature of the fluid guided within the lumen.

A basic idea of the invention is, in conventional measuring systems of the type being discussed, not least by all also in conventional vibronic measuring systems, in the case of ascertaining measured values for a particular target temperature, for example, namely a tube temperature and/or a measured fluid temperature, respectively also in the case of ascertaining measured values for the density and/or the viscosity, to register in a manner accessible for measuring, respectively metrological, processing, an influence of a temperature difference existing between the measured fluid temperature, respectively the tube temperature, on the one hand, and the tube ambient temperature, on the other hand, and regularly additionally also fluctuating over a broad temperature range. This is done by using two temperature sensors thermally well, equally as well differently strongly, coupled to the tube of the transducer apparatus and/or differently strongly coupled to the fluid volume surrounding the tube, so that, as a result,—in the case of nominally equal temperature differences falling across the temperature sensors—the temperature measurement location formed by means of the first of the two temperature sensors assumes a measurement location temperature, which differs from a measurement location temperature of the temperature measurement location formed by means of the second of the two temperature sensors. Knowing the thermal resistances related by the respectively designed construction of the two temperature sensors, consequently their earlier very exactly known sizes, respectively ratios, respectively relevant for the heat conduction processes through the temperature sensors, and based on the so forced deviation of the two measurement location temperatures from one another, then the temperature difference existing between the measured fluid temperature and the tube ambient temperature, respectively based thereon, the particular target temperature, for example, namely the tube temperature or also the measured fluid temperature, can be exactly ascertained.

BRIEF DESCRIPTION OF THE DRAWINGS

The invention as well as other advantageous embodiments thereof will now be explained in greater detail based on the examples of embodiments shown in the figures of the drawing. Equal parts are provided in all figures with equal reference characters; when perspicuity requires or it otherwise appears sensible, already mentioned reference characters are omitted in subsequent figures. Other advantageous embodiments or further developments, especially also combinations of, first of all, only individually explained aspects the invention, result, furthermore, from the figures of the drawing, as well as also the dependent claims per se. The figures of the drawing show as follows:

DETAILED DISCUSSION IN CONJUNCTION WITH THE DRAWINGS

Figure 1:
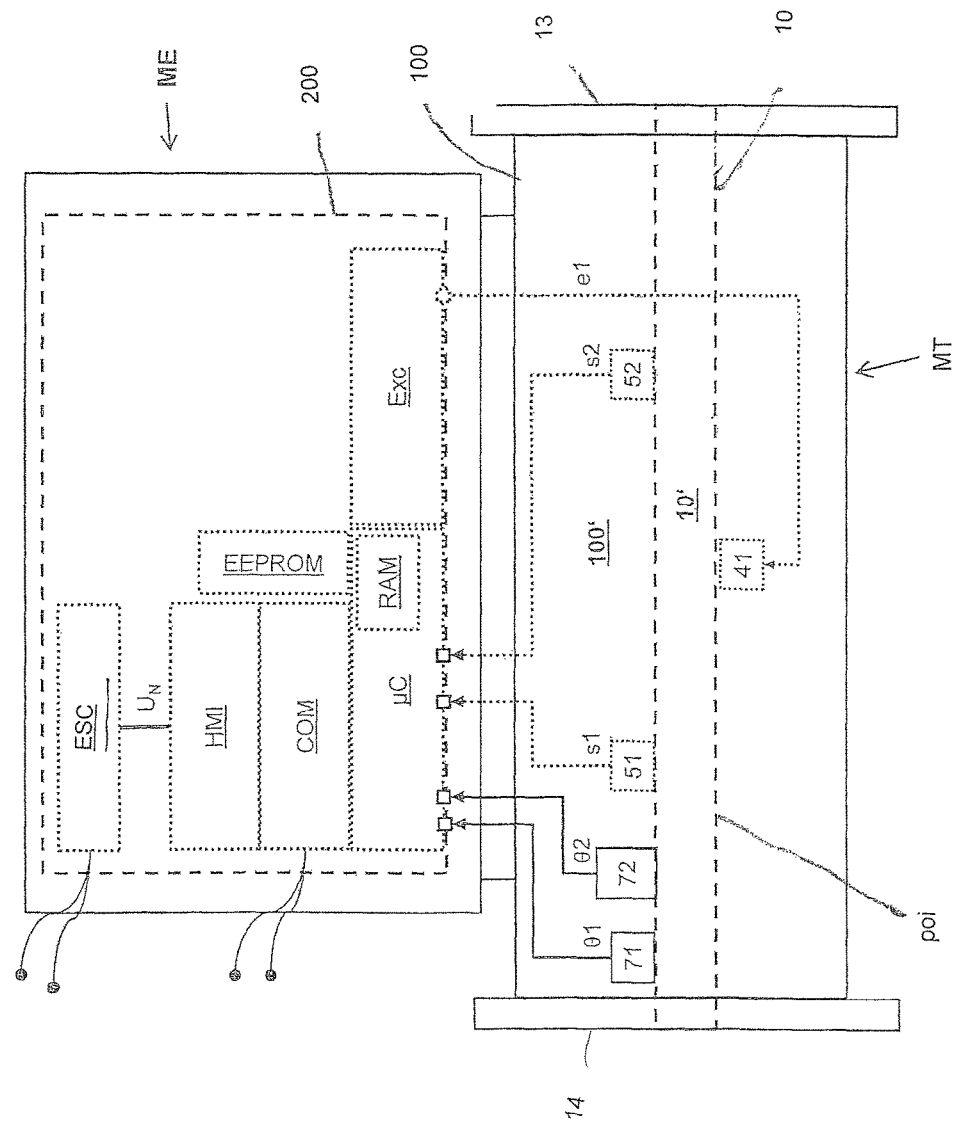
FIG. 1 shows schematically, an example of an embodiment of a measuring system, especially a measuring system suitable for application in industrial measuring and automation technology, wherein the measuring system comprises: a transducer apparatus having a transducer housing; and a measuring and operating electronics accommodated in an electronics housing here an electronics housing secured directly on the transducer housing.

FIG. 1 shows schematically a measuring system for measuring at least one measured variable x of a flowing fluid FL1 (measured fluid), such as e.g. a gas, a liquid or a flowable dispersion, having a measured fluid temperature $\vartheta_{FL1}$, which may, in given cases, also be time variable. The measuring system serves for recurringly ascertaining measured values $X_x$ instantaneously representing the measured variable. Measured variable x can be, for example, a density or a viscosity, consequently a measured variable, which has a certain dependence on the respective measured fluid temperature and/or in the case of whose conversion into the respective measured value $X_x$ the transducer apparatus causes a temperature dependent measuring error. The measured variable can, however, also be, for example, a temperature (henceforth also referred to as target temperature) of interest at an apparatus reference point (poi) predetermined for the measuring system and located within the transducer apparatus. The measuring system comprises a transducer apparatus MT for producing measurement signals dependent on the at least one measured variable as well as a measuring and operating electronics ME electrically connected with such and especially during operation supplied from the outside via connection cable and/or by means of an internal energy storer with electrical energy, and serving for producing the measured values representing the measured variable(s) registered by means of the transducer apparatus, respectively for sequentially outputting to a corresponding to measurement output such measured values as currently valid measured values of the measuring system.

The measuring and operating electronics ME, formed e.g. by means of at least one microprocessor and/or by means of a digital signal processor (DSP), can, such as indicated in FIG. 1, be accommodated, for example, in a single, in given cases, also chambered, electronics housing 200 of the measuring system. The electronics housing 200 can, depending on demands on the measuring system, be embodied, for example, also impact- and/or also explosion resistantly and/or hermetically sealedly. The measuring device electronics ME includes, as well as also shown schematically in FIG. 1 in the manner of a block diagram, an evaluating circuit μC processing measurement signals of the transducer apparatus MT and formed, for example, by means of a microprocessor. During operation, the evaluating circuit μC generates corresponding measured values for the measured variable to be registered by means of the measuring system. The measured values $X_x$ generated by means of the measuring and operating electronics ME can, in the case of the measuring system shown here, be displayed, for example, on-site, namely directly at the measuring point formed by means of the measuring system. For visualizing, on-site, measured values produced by means of the measuring system and/or, in given cases, measuring device internally generated, system status reports, such as, for instance, a report signaling increased measurement accuracy, respectively error, or an alarm signaling a disturbance in the measuring system or at the measuring point formed by means of the measuring system, the measuring system can, as well as also indicated in FIG. 1, have, for example, a display- and servicing element HMI communicating with the measuring and operating electronics, in given cases, also a portable, display- and servicing element HMI, such as, for instance, an LCD-, OLED- or TFT display located in the electronics housing 200 behind a window correspondingly provided therein as well as a corresponding input keypad and/or touch screen. In advantageous manner, the, for example, also (re-)programmable-, respectively remotely parameterable, measuring and operating electronics ME can additionally be so designed that it can, during operation of the measuring system, exchange with an electronic data processing system superordinated thereto, for example, a programmable logic controller (PLC), a personal computer and/or a work station, via a data transmission system, for example, a field bus system, such as, for instance, FOUNDATION FIELDBUS, PROFIBUS, and/or wirelessly per radio, measuring—and/or other operating data, such as, for instance, current measured values, system diagnostic values, system status reports or, however, also setting values serving for control of the measuring system.

The measuring- and evaluating circuit μC of the measuring and operating electronics can be implemented, for example, by means of at least one microprocessor and/or microcomputer having a digital signal processor (DSP). The program codes to be executed thereby, as well as also operating parameters serving for control of the respective measuring system, such as e.g. also desired values for control algorithms, implemented by means of the measuring and operating electronics can —, such as also schematically shown in FIG. 1 —, e.g. be stored persistently in a non-volatile data memory EEPROM of the measuring and operating electronics ME and be loaded at startup of the same into a volatile data memory RAM, e.g. one integrated into the microcomputer. Microprocessors suitable for such applications are available from the firm Texas Instruments Inc., an example being type TMS320VC33.

Furthermore, the measuring and operating electronics ME can be so designed that it can be fed from an external energy supply, for example, also via the aforementioned fieldbus system. For such purpose, the measuring and operating electronics ME can have, for example, an internal energy supply circuit ESC for providing internal supply voltages UN. During operation, the energy supply circuit ESC is fed via the aforementioned fieldbus system by an external energy supply provided in the aforementioned data processing system. In such case, the measuring system can be embodied, for example, as a so-called four conductor device, in the case of which the internal energy supply circuit of the measuring device electronics ME can be connected by means of a first pair of lines with an external energy supply and the internal communication circuit of the measuring and operating electronics ME can be connected by means of a second pair of lines with an external data processing circuit or an external data transmission system. The measuring and operating electronics can, furthermore, however, also be so embodied that it is, such as also shown, among others, in the above mentioned U.S. Pat. Nos. 7,200,503, and 7,792,646, electrically connectable with the external electronic data processing system by means of a two-conductor connection, configured, for example, as a 4-20 mA electrical current loop, and via that both is supplied with electrical energy as well as also measured values can be transmitted to the data processing system. For the typical case, in which the measuring system is provided for coupling to a field bus- or other electronic communication system, the measuring and operating electronics ME, which is, for example, also (re-) programmable on-site and/or via a communication system, can additionally have a corresponding communication interface COM, for example, one conforming to relevant industry standards, such as, for instance, IEC 61158/IEC 61784, for data communication, e.g. for sending measuring- and/or operating data, thus the measured values representing the particular measured variable, to the above mentioned programmable logic controller (PLC) or to a superordinated process control system and/or for receiving settings data for the measuring system. The electrical connecting of the transducer apparatus to the measuring and operating electronics can occur by means of corresponding connecting lines, which run from the electronics housing 200, for example, via an electrical cable feedthrough, into the transducer housing 100 and at least sectionally also within the transducer housing 100. The connecting lines can, in such case, be embodied at least partially as line wires at least sectionally encased by electrical insulation, e.g. in the form of "twisted pair" lines, flat ribbon cables and/or coaxial cables. Alternatively thereto or in supplementation thereof, the connecting lines can be formed at least sectionally also by means of conductive traces of a, for example, flexible, respectively partially rigid and partially flexible, in given cases also lacquered, circuit board; compare for this also the above mentioned US-A 2001/0037690 or WO-A 96/07081.

Figure 2:
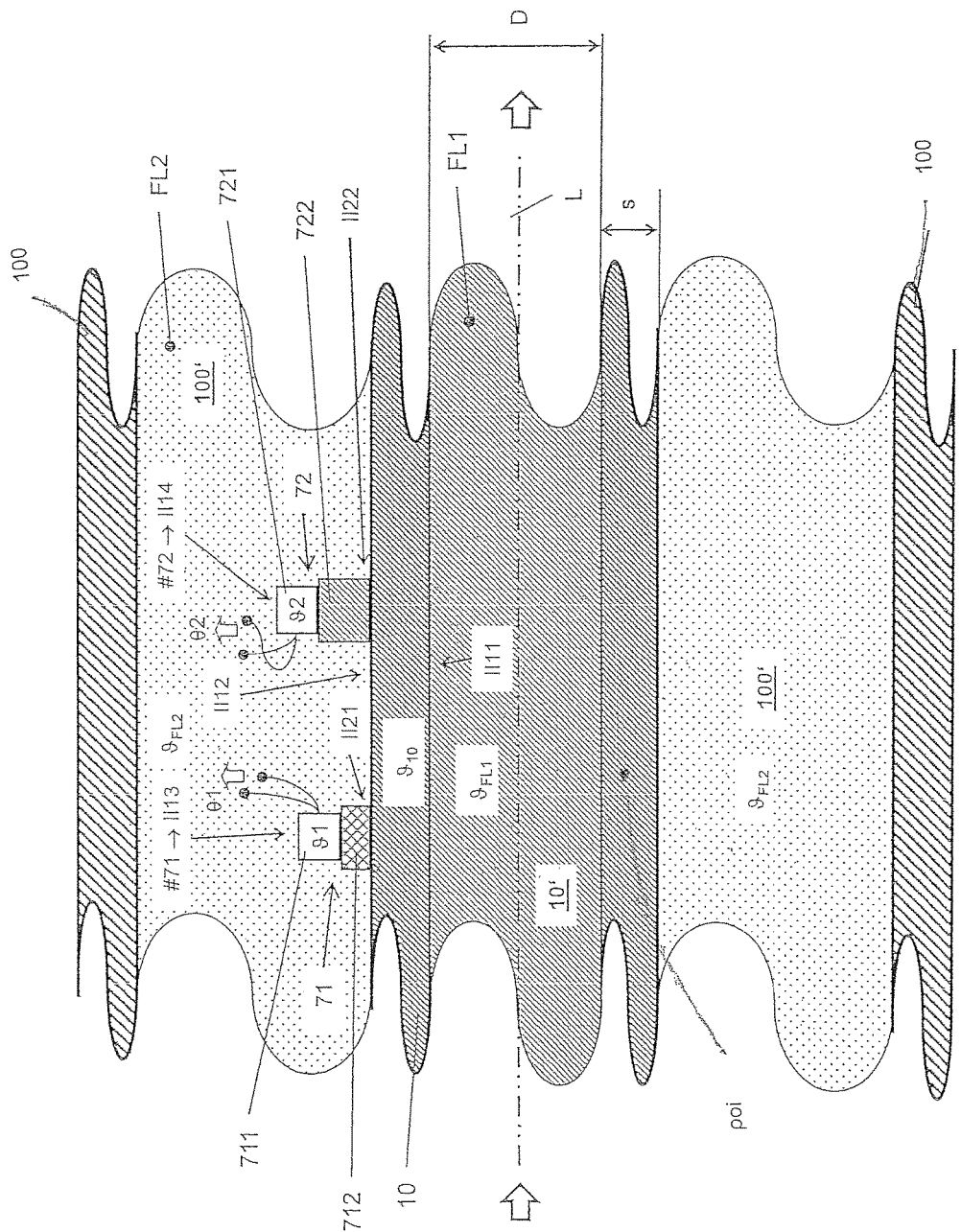
FIGS. 2 and 3 show differently sectioned views of examples of embodiments of a transducer apparatus suitable for a measuring system of FIG. 1 and comprising a tube and two temperature sensors secured thereto and contacting the wall of the tube.

The transducer apparatus of the measuring system serves—such as schematically shown in FIG. 2, respectively evident from a combination of FIGS. 1 and 2—, especially to guide during operation a volume portion of the respective fluid FL1 to be measured, respectively serves to be flowed through by the fluid, as well as to provide different measurement signals for physical measured variables respectively to be registered by means of the transducer apparatus, especially namely for measurement location temperatures reigning at different measurement points within the transducer apparatus. The transducer apparatus includes a transducer housing 100 as well as a therein accommodated tube 10 having a lumen 10' surrounded by a wall, for example, a metal wall, wherein the tube 10 is arranged within a cavity of the transducer housing surrounded by a wall of the transducer housing, for example, a metal wall and/or a wall serving as an outer protective shell, in such a manner that between an inner surface 100+ of the wall of the transducer housing 100 facing the cavity and a outer surface 10# of the wall of the tube 10, namely an outer surface of the wall of the tube 10 facing the cavity, an intermediate space 100' is formed. Tube 10 is, especially, adapted to guide in its lumen the fluid FL1 (respectively, a volume portion thereof) in such a manner that an inner surface 10+ of the wall of the tube facing the lumen is contacted by fluid FL1 guided in the lumen to form a first interface II11 of a first type, namely an interface between a fluid and a solid phase, whereby, as a result, a tube temperature $\vartheta_{10}$, namely a temperature assumed by the wall of the tube 10, is co-determined also by the measured fluid temperature $\vartheta^{FL1}$ of the fluid FL1 instantaneously located in the lumen.

The transducer apparatus can, furthermore, be embodied as a measuring transducer of a vibration-type, such as applied, for example, in a vibronic measuring system formed as a Coriolis mass flow measuring device, as a density measuring device and/or as a viscosity measuring device, respectively as a component of such a measuring transducer. Accordingly, the tube is in an additional embodiment of the invention, furthermore, adapted to be flowed through by the fluid FL1 and during that to be caused to vibrate; this, for example, in such a manner that the tube executes mechanical oscillations about a static resting position associated therewith, oscillations which are suitable to induce in the flowing fluid Coriolis forces dependent on a mass flow rate m and/or frictional forces dependent on a viscosity η and/or inertial forces dependent on a density ρ. Particularly for this case, the transducer apparatus is according to an additional embodiment of the invention, furthermore, equipped with an oscillation exciter 41 for exciting and maintaining mechanical oscillations of the at least one tube about an associated static resting position, as well as at least one oscillation sensor 51 for registering mechanical oscillations of the at least one tube and for generating an oscillation measurement signal s1 representing oscillatory movements of the tube. For this case, in which the transducer apparatus is embodied as a measuring transducer of a vibration-type, respectively as a component thereof, there is provided in the measuring and operating electronics ME, furthermore, a corresponding driver circuit Exc, namely one serving for activating the transducer apparatus and, in given cases, also electrically connected with the measuring and evaluating circuit μC, which driver circuit Exc is adapted to provide at least one electrical driver signal e1 for an oscillation exciter provided, in given cases, in the transducer apparatus. Finally, the measuring and operating electronics can for this case also be so embodied that it corresponds as regards circuit construction to one of the measuring and operating electronics known from the above mentioned state of the art, for example, for instance, U.S. Pat. No. 6,311,136, or, for example, also to a measurement transmitter of a Coriolis mass flow/density measuring device sold by the applicant, e.g. under the designation "PROMASS 83F", respectively described at http://www.de.endress.com/#product/83F.

Tube 10 of the transducer apparatus of the invention can be embodied to be at least sectionally straight, consequently sectionally (hollow-)cylindrical, for example, namely circularly cylindrical, and/or at least sectionally curved, for example, namely curved in the form of a circular arc shape. In the example of an embodiment shown here, the—here predominantly, respectively completely, straight—tube, consequently the transducer apparatus formed therewith, is, furthermore, adapted to be inserted into the course of a process line, for example, one formed as a rigid pipeline, guiding the fluid. Especially, the transducer apparatus is, furthermore, adapted to be connected releasably with the process line, for example, a process line in the form of a metal pipeline. For such purpose, there are provided on the inlet side of the transducer apparatus a first connecting flange 13 serving for connecting the tube to a line segment of the process line supplying the fluid FL1 and on the outlet side of the transducer apparatus a second connecting flange 14 serving for connecting the tube to a line segment of the process line draining the fluid. The connecting flanges 13, 14 can, in such case, such as quite usual in the case of transducer apparatuses of the type being discussed, also be integrated terminally in the transducer housing 100, namely be embodied as an integral component of the transducer housing.

In an additional embodiment of the invention, it is, furthermore, provided that the wall of the tube is composed at least partially —, for example, also predominantly or completely—of a material, whose specific thermal conductivity $\lambda 10$ is greater than 10 W/(m·K) and whose specific heat capacity cp10 is less than 1000 J/(kg·K). As already indicated, the wall can be, for example, of a metal, respectively a metal alloy, for example, namely titanium, zirconium or tantalum, respectively a corresponding alloy thereof, a steel or a nickel based alloy. Furthermore, it is provided that the wall of the tube according to an additional embodiment of the invention has a wall thickness s, which amounts to more than 0.5 mm, and/or an inner diameter, which amounts to more than 0.5 mm. Alternatively or supplementally, the tube is, furthermore, so dimensioned that it has an inner diameter to wall thickness ratio D/s, defined as a ratio of an inner diameter D of the tube to a wall thickness s of the wall of the tube, which amounts to less than 25:1. In an additional embodiment of the invention, it is, furthermore, provided that the wall thickness amounts to less than 10 mm and/or the inner diameter D amounts to less than 200 mm, respectively that the tube is so dimensioned that the inner diameter to wall thickness ratio D/s amounts to more than 5:1.

For registering measurement location temperatures reigning within the transducer apparatus and for converting the same into a respective temperature measurement signal, the transducer apparatus of the invention comprises—such as shown in FIG. 1, respectively 2—, furthermore, a first temperature sensor 71 as well as a second temperature sensor 72. Temperature sensor 71 is —, such as schematically shown in FIG. 2—formed by means of a first temperature detector 711 arranged within the intermediate space 100' as well as by means of a first coupling body 712 coupling the temperature detector 711 thermally conductively with the wall of the tube and additionally adapted to transduce a first measurement location temperature $\vartheta 1$, namely a temperature at a first temperature measurement location formed by means of the temperature detector 711, into a first temperature measurement signal $\theta 1$, namely a first electrical measurement signal representing the measurement location temperature 91. Analogously thereto, the temperature sensor 72 of the transducer apparatus of the invention is formed by means of a second temperature detector 721 likewise arranged within the intermediate space 100' —, for example, also constructed equally to the temperature detector 711—as well as by means of a second coupling body 722 coupling the temperature detector 721 thermally conductively with the wall of the tube, as well as adapted to transduce a second measurement location temperature $\vartheta 2$, namely a temperature at a second temperature measurement location formed by means of the temperature detector 721, into a second temperature measurement signal $\theta 2$, namely a second electrical measurement signal representing the measurement location temperature Each of the temperature measurement signals $\theta 1$, $\theta 2$ can, for example, be so embodied that it has an electrical signal voltage dependent on the respective measurement location temperature and/or an electrical signal current dependent on the measurement location temperature. Moreover, the measuring and operating electronics ME is, according to an additional embodiment of the invention, adapted to generate the at least one measured value $X_x$ using both the first temperature measurement signal $\theta 1$ generated by means of the transducer apparatus as well as also at least the second temperature measurement signal $\theta 2$ generated by means of the transducer apparatus.

Each of the two temperature detectors 711, 721 can be formed, for example, by means of a platinum measuring resistor, a thermistor or a thermocouple. Furthermore, each of the temperature detectors 711, 721 can be connected with the respectively associated coupling body 712, respectively 722, by means of a suitable material bonded connection, for example, namely an adhesive connection or a soldered, brazed or welded connection, and/or by being embedded in the respective coupling body 712, respectively 722.

In an additional embodiment of the invention, the two temperature sensors 71, 72 are, furthermore, so positioned that the first temperature sensor 71 and the second temperature sensor 72 are, as shown in FIG. 2, axially spaced with reference to an imaginary longitudinal axis L of the tube, respectively a straight tube segment thereof, so that thus, as a result, the tube has no imaginary, circular peripheral line, which lies in the outer surface 10# and along which line both the first temperature sensor as well as also the second temperature sensor are positioned. Alternatively thereto or in supplementation thereof, the two temperature sensors can, furthermore, also be so positioned that the temperature sensor 71 and the temperature sensor 72 —, as well as also indicated in FIG. 3—are spaced with reference to the longitudinal axis L of the tube, respectively a straight tube segment thereof, azimuthally —, for example, lying diametrically opposite one another.

Figure 4:
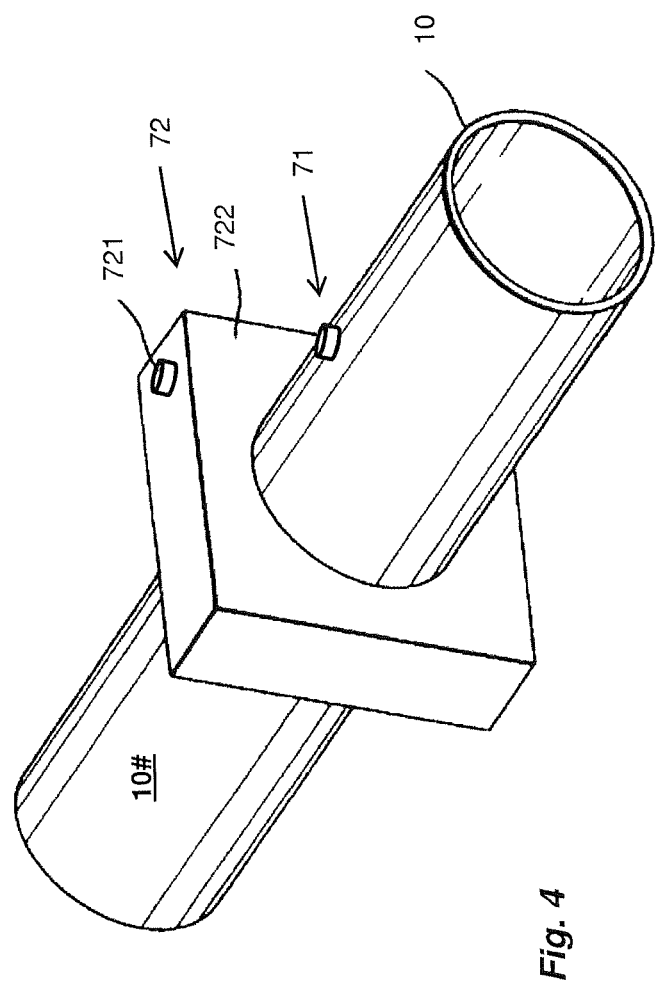
FIGS. 4 and 5 show in perspective, respectively sectioned, views of a tube suitable for a transducer apparatus of FIG. 2, respectively 3, consequently suitable for a measuring system of FIG. 1, and having two temperature sensors secured thereto.
Figure 5:
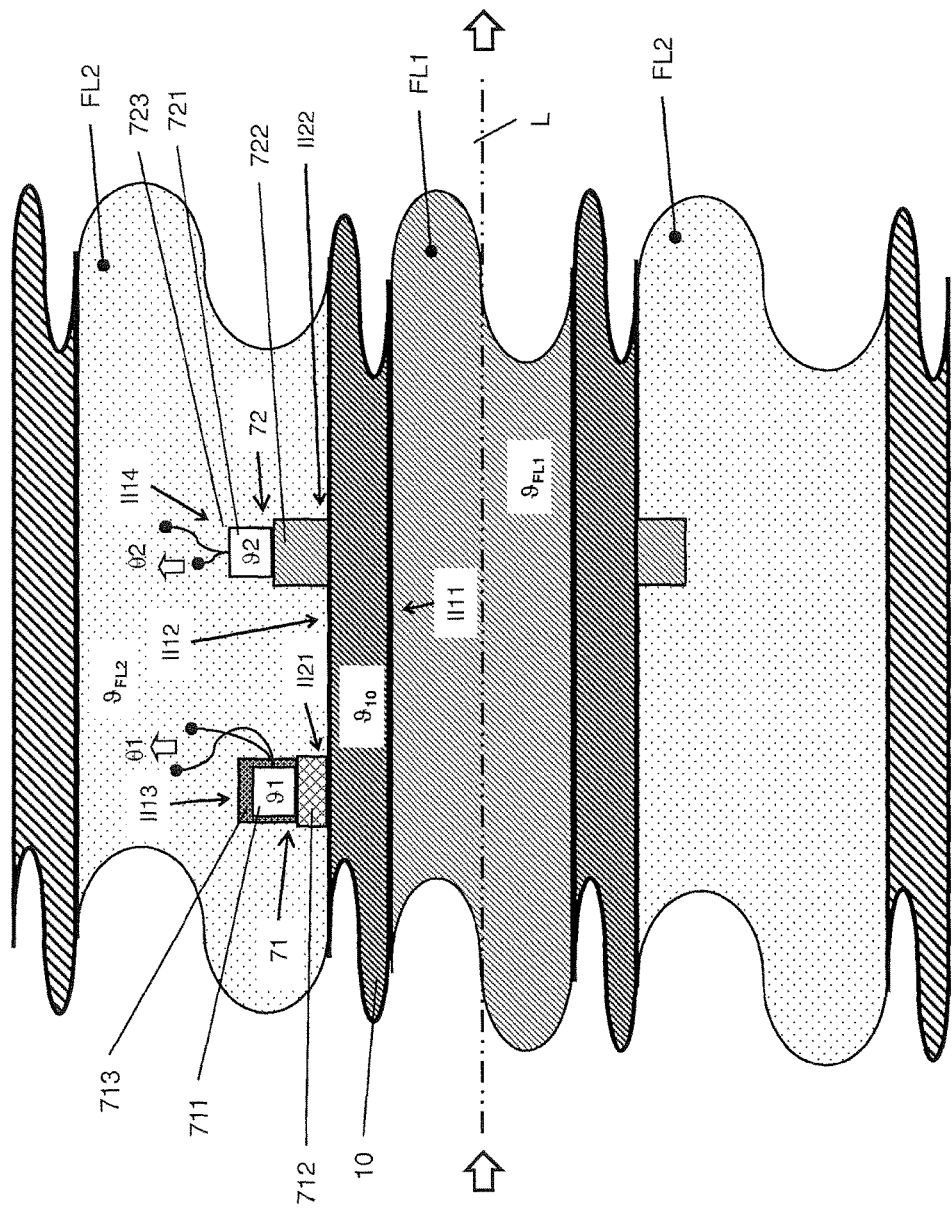

For the purpose of achieving a mechanically fixed and resistant, equally as well thermally well conductive connection between the wall of the tube and the temperature sensor 71, this is according to an additional embodiment of the invention connected with the outer surface 10# of the wall of the tube 10 by the bonding of materials, for example, namely adhesively or by means of a soldered, brazed, respectively welded connection. Serving for manufacturing such a material bonded connection between tube 10 and temperature sensor 71, can be e.g. a thermally conductive adhesive, consequently a synthetic material based on epoxide resin or based on silicone, for example, namely a silicone elastomer or a 1- or 2-component silicone rubber, such as sold by, among others, also the firm, DELO Industrial Adhesives GmbH & Co KGaA, 86949 Windach, Germany, under the name DELO-GUM® 3699. The synthetic material applied for connecting temperature sensor 71 and tube 10 can for the purpose of achieving an as good as possible heat conduction additionally also be mixed with metal oxide particles. Furthermore, it is additionally also possible to manufacture the coupling body 712—partially or completely—of synthetic material, for example, also in such a manner that a plastic molded part located between the temperature detector 711 and the wall, respectively contacting both the outer surface 10# of the wall as well as also the temperature detector 711, in given cases, also a monolithic molded part, serves as coupling body 712, respectively the entire coupling body 712 is composed of synthetic material—, for example, singly or multiply applied to the wall of the tube 10, and, consequently, located between the wall of the tube and the first temperature detector 711. Moreover, also the temperature sensor 72 can be connected with the outer surface 10# of the wall of the tube 10 by the bonding of materials, for example, namely in the form of an adhesive or soldered, brazed or welded connection. For such purpose, the coupling body 722 according to an additional embodiment of the invention is composed at least partially, for example, also predominantly, of a metal. Consequently, the coupling body 722 can be produced of a material, which has a specific thermal conductivity λ2 greater than 10 W/(m·K) and/or a specific heat capacity cp722 less than 1000 J/(kg·K). Furthermore, the two coupling bodies 712, 722 can by corresponding selection of the materials respectively actually used for their respective manufacture be directly so embodied that the specific thermal conductivity λ722 of a material of the second coupling body 722 is greater than a specific thermal conductivity λ712 of a material of the first coupling body 712 and/or the specific heat capacity cp722 of the material of the second coupling body 722 is less than a specific heat capacity cp712 of the material of the first coupling body 712. In another embodiment of the invention, also the second coupling body 722 of the temperature sensor 72 is at least partially produced of a synthetic material, respectively formed by means of a plastic body correspondingly located between the temperature detector 721 and the wall of the tube. Alternatively thereto or in supplementation thereof, according to an additional embodiment of the invention, it is provided that the coupling body 722 of the temperature sensor 72—, as well as also indicated in FIG. 4 or 5, respectively directly evident from their combination—is formed by means of a disk located between the wall of the tube 10 and the temperature detector 721 and composed of a metal, respectively a metal alloy, for example, a steel. The disk can be embodied as a washer having a passageway matched to the outer surface of the wall of the tube—, for example, be essentially annular or, as well as also shown schematically in FIG. 4, be essentially rectangular —, so that it can be pushed onto the tube, in such a manner that the disk grips around the tube, respectively an inner surface of the passageway facing the outer surface of the tube at least partially contacts the outer surface 10# of the wall of the tube. Particularly for the above-described case, in which the transducer apparatus is embodied as a measuring transducer of vibration-type, respectively a component thereof, the washer can, for example, serve both as a coupling body 722 of the temperature sensor 72, respectively as a part thereof, as well as also as a node plate forcing oscillation nodes of mechanical oscillations of the tube or, however, for example, also as a holder also of the mentioned oscillation sensor 51.

Figure 3:
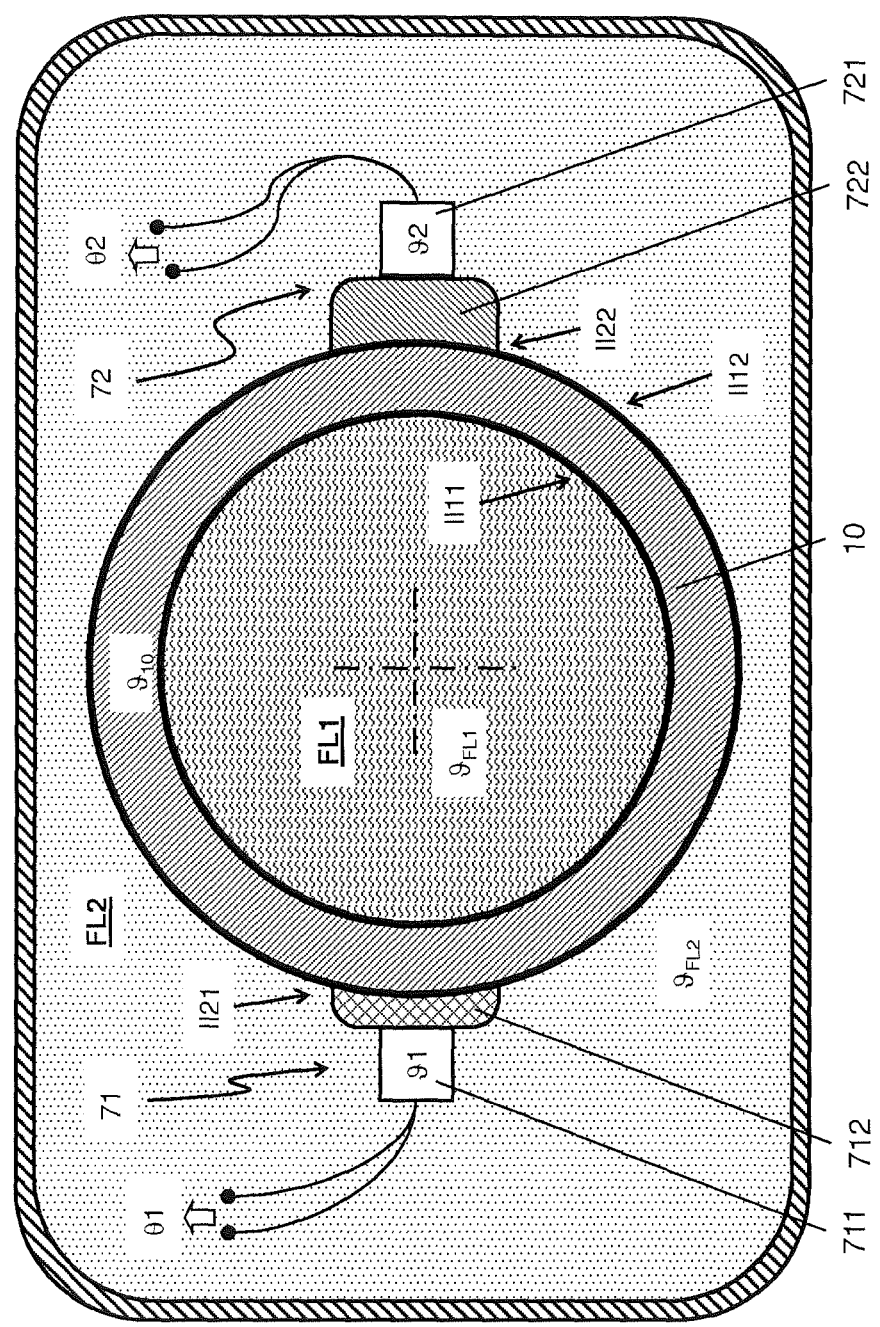

As shown schematically in FIG. 2, respectively FIG. 3, the two temperature sensors are thermally coupled to the tube. Thus, the coupling body 712 of the temperature sensor 71 contacts the outer surface 10# of the wall of the tube to form a first interface II21 of a second type, namely an interface between two solid phases, and the coupling body 722 of the temperature sensor 72 contacts the outer surface 10# of the wall of the tube to form a second interface II22 of a second type. Each of the two interfaces II21, II22 has, in such case, a surface area related to, consequently predetermined by, the particular form of construction of the respective coupling body 712, respectively 722. Accordingly, as shown in simplified manner in FIG. 6 based on an equivalent circuit for a resistor network formed by means of a plurality of discrete thermal resistances, a first thermal resistance R1 (R1=ΔT1/Q1) thermally conductively connected with the first temperature measurement location—here a first thermal resistance principally determined by heat conduction —, opposes a heat flux Q1 resulting from a temperature difference ΔT1 reigning between the interface II21 of a second type and the first temperature measurement location, equally as well a heat flux Q1 totally passing through interface II21 and further flowing on to the first temperature measurement location, and a second thermal resistance R2 (R2=ΔT2/Q2) thermally conductively connected with the second temperature measurement location—here a second thermal resistance likewise principally determined by heat conduction —, opposes a heat flux Q2 resulting from a temperature difference ΔT2 reigning between the interface II22 of second type and the second temperature measurement location, equally as well totally passing through interface II22 and further flowing on to the second temperature measurement location. In order to achieve an as good as possible thermal coupling of the temperature sensor 71, as well as also the temperature sensor 72, to the wall of the tube, each of the thermal resistances R1 and R2, respectively each of the temperature sensors 71, 72, is, according to an additional embodiment of the invention, so dimensioned that each of the thermal resistances R1 and R2 is less than 1000 K/W. Furthermore, at least the thermal resistance R1, respectively the temperature sensor 71, is also so dimensioned that the thermal resistance R1 is less than 30 K/W, especially less than 25 K/W.

Figure 6:
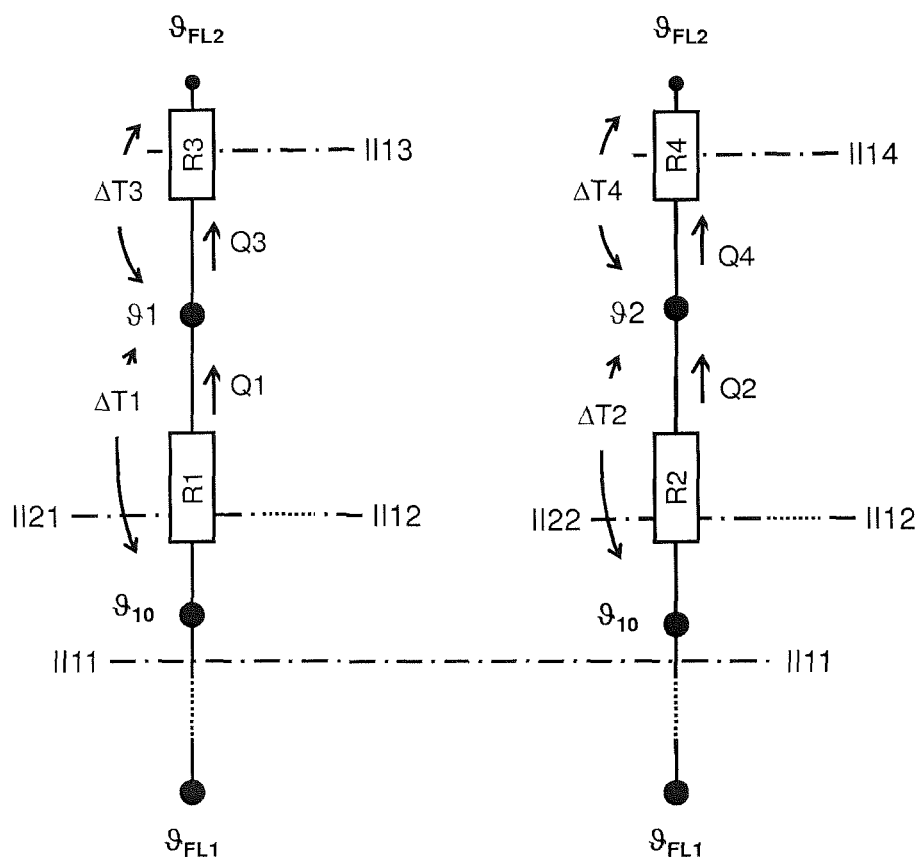
FIG. 6 shows a resistor network formed by means of a plurality of discrete thermal resistances in the manner of an equivalent circuit, serving for explaining heat fluxes in a transducer apparatus of FIG. 2, 3, respectively corresponding temperature drops within the transducer apparatus.

In order that each of the temperature sensors 71, 72 —, as well as also assumed in the case of the (static) calculation model underpinning the equivalent circuit diagram shown in FIG. 6 —, has only a comparatively low, consequently negligible, thermal inertia, respectively each of the two measurement location temperatures can quickly follow possible changes of the tube temperature $\vartheta_{10}$, respectively that, conversely, each of the two measurement location temperatures is not or, at most, in only small measure, dependent on a rate of change of the tube temperature $\vartheta_{10}$, namely a velocity, with which the tube temperature changes as a function of time, it is, according to an additional embodiment of the invention, furthermore, provided that each of the coupling body 712 and 722 is so constructed that both the coupling body 712 as well as also the coupling body 722 has a heat capacity C1, respectively C2, which is less than 2000 J/K; this advantageously, furthermore, such that the heat capacity C1 of the first coupling body 712 and the heat capacity C2 of the second coupling body 722 fulfill a condition $$\frac{1}{1000} < \frac{C1}{C2} \leq 1,$$

and/or that at least the coupling body 712 has a specific heat capacity, which is less than 200 J/(kg·K), preferably, however, also less than 100 J/(kg·K). Due to the compact construction typically desired for temperature sensors of the type being discussed, as well as the typically used, namely thermally very conductive, materials, there is additionally also a close relationship between thermal resistance and heat capacity of the respective temperature sensors, in such a manner that the particular heat capacity—consequently also the above-mentioned heat capacity C1, respectively C2—is ever lower, depending on how low the particular thermal resistance is selected. Accordingly, by dimensioning the thermal resistances R1, R2 of the coupling body 712, respectively 722 in the above indicated manner, thus, simultaneously, it can also be achieved that each of the temperature sensors 71, 72 also has only a comparatively low thermal inertia relative to the tube temperature $\vartheta_{10}$, respectively each of the two measurement location temperatures—such as desired—, can, in each case, quickly follow possible changes of the tube temperature $\vartheta_{10}$, respectively, conversely, that each of the two measurement location temperatures is not or, at most, in only small measure, dependent on a rate of change of the tube temperature $\vartheta_{10}$, namely a velocity, with which the tube temperature $\vartheta_{10}$ changes as a function of time.

The intermediate space 100' formed between the inner surface 100+ of the wall of the transducer housing 100 and the outer surface 10# of the wall of the tube 10 is, furthermore,—such as quite usual in the case of transducer apparatuses of the type being discussed and such as indicated in FIG. 2, respectively 3, in each case, schematically by means of the stippling—filled with a fluid FL2, for example, a fluid FL2 having a specific thermal conductivity $\lambda F$ of less than 1 W/(m·K), for the purpose of forming a fluid volume surrounding the tube 10. The fluid FL2 in the intermediate space 100', respectively the fluid volume formed therewith, has a fluid temperature, henceforth referred to as the tube ambient temperature $\vartheta_{FL2}$, in given cases, also a time variable fluid temperature, which, at least at times, deviates from the measured fluid temperature $\vartheta_{FL1}$ by more than 1 K (Kelvin), especially at least at times by more than 5 K. Accordingly, in an additional embodiment of the invention, the transducer housing and the tube are adapted to hold the fluid FL2 in the intermediate space 100' in such a manner that the outer surface 10+ of the wall of the tube facing the intermediate space 100' is contacted by fluid FL2 held in the intermediate space to form a second interface II12 of a first type, consequently the tube is thermally coupled to the fluid volume formed in the intermediate space 100'. Serving as fluid FL2 can be, for example, air or an inert gas, such as e.g. nitrogen or a noble gas, especially helium. As a result of this, also an outer surface of the temperature sensor 71 facing the intermediate space 100' is contacted by fluid FL2 held in the intermediate space to form a third interface II13 of a first type (interface between a fluid and a solid phase) as well as an outer surface of the temperature sensor 72 equally facing the intermediate space 100' is contacted by fluid FL2 held in the intermediate space to form a fourth interface II14 of a first type, respectively both the temperature sensor 71 as well as also the temperature sensor 72 are thermally coupled to the fluid volume formed in the intermediate space 100' in such a manner that—, as well as also schematically shown in FIG. 2, respectively 3—a third thermal resistance R3 (R3=ΔT3/Q3) thermally conductively connected with the first temperature measurement location—here namely a third thermal resistance determined by heat conduction, as well as also by heat flow (convection) occurring at the interface II13—opposes a heat flux Q3 resulting from a temperature difference ΔT3 reigning between the interface II13 of a first type and the first temperature measurement location, namely a heat flux flowing from the first temperature measurement location totally to the interface II13, equally as well totally passing through the interface II13 and a fourth thermal resistance R4 (R4=ΔT4/Q4) thermally conductively connected with the second temperature measurement location—here a fourth thermal resistance likewise determined by heat conduction as well as heat flow occurring at the interface II14—opposes a heat flux Q4 resulting from a temperature difference ΔT4 reigning between the interface II14 of a first type and the second temperature measurement location, namely a heat flux flowing from the second temperature measurement location totally to the interface II14, equally as well totally passing through the interface II14. Each of the thermal resistances R3 and R4 is advantageously so dimensioned that it is less than 20000 K/W, especially less than 10000 K/W. In order to achieve an, in comparison to the thermal coupling to the tube 10, weaker thermal coupling of the temperature sensor 71, respectively of the temperature sensor 72, to the fluid volume formed in the intermediate space 100', not least of all also to achieve that the measurement location temperature 41, respectively 42, registered therewith is as immune as possible to rapid changes of the ambient temperature $\vartheta_{FL2}$ of the tube as a function of time —, in given cases, also spatially different changes —, respectively that the temperature sensors have relative to the ambient temperature $\vartheta_{FL2}$ of the tube an as much as possible greater thermal inertia than is the case relative to the tube temperature $\vartheta_{10}$, the temperature sensor 71, respectively the temperature sensor 72, are, according to an additional embodiment of the invention, furthermore, so embodied that the thermal resistance R3, respectively the thermal resistance R4, amounts to more than 500 K/W, especially more than 5000 K/W.

Figure 7:
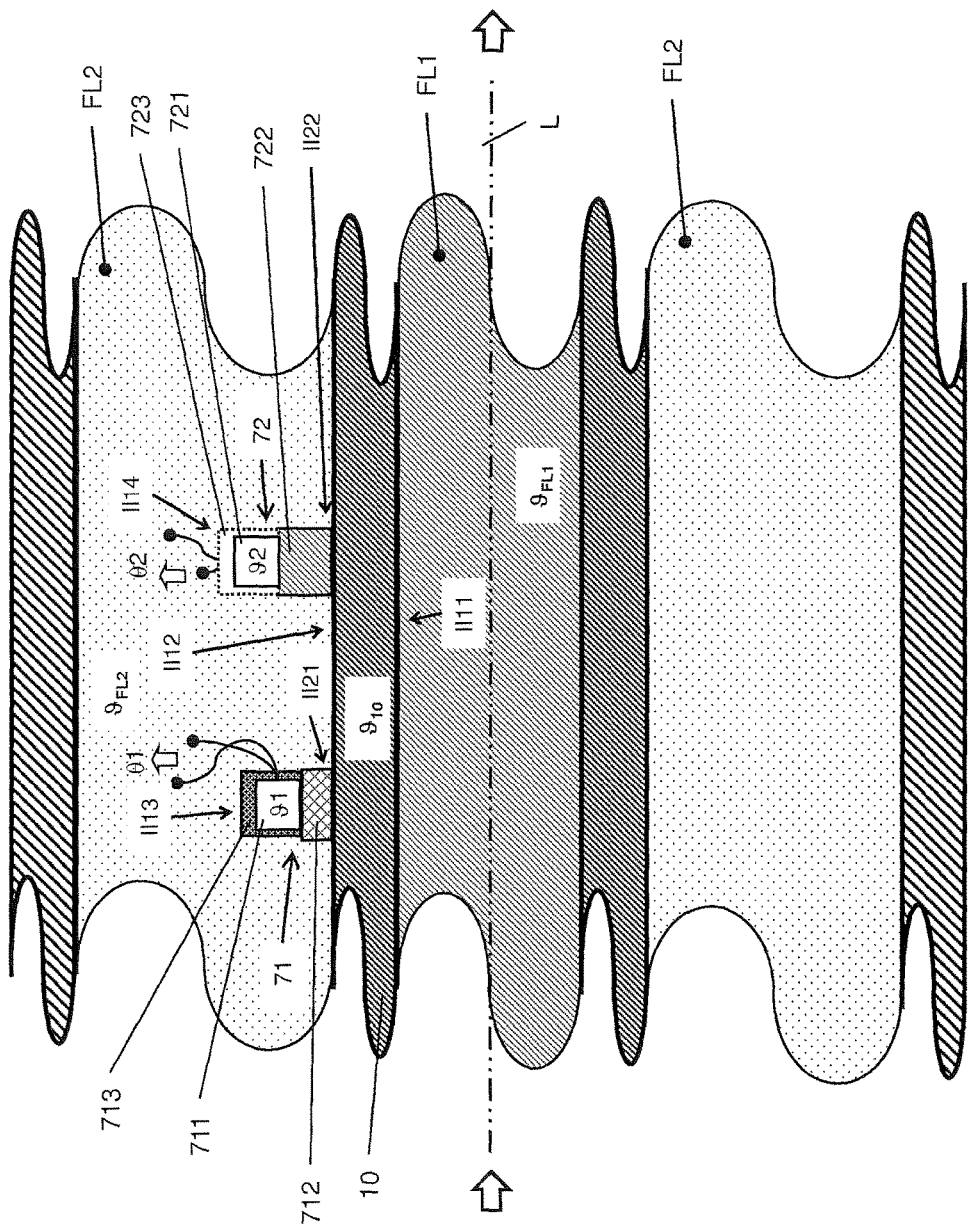
FIGS. 7 and 8 shown in differently sectioned views, other examples of embodiments of tube and transducer apparatus suitable for a measuring system of FIG. 1.
Figure 8:
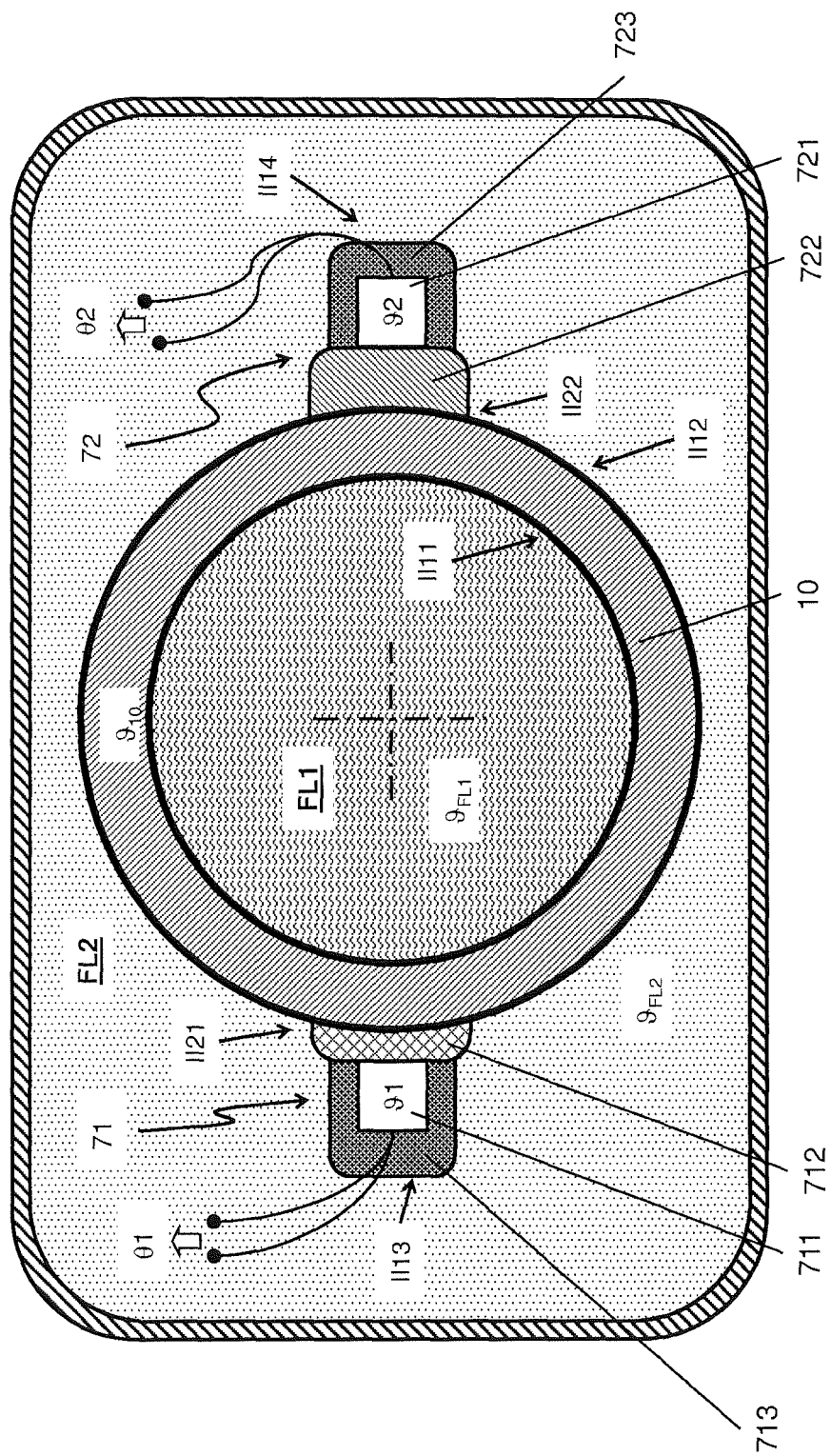

In order, on the one hand, to be able to determine the thermal resistance R3 earlier as simply as possible, on the other hand, however, also to be able so to construct the thermal resistance R3 that its particular examples within a batch, respectively a series, of industrially manufactured transducer apparatuses of the type being discussed have from transducer apparatus to transducer apparatus also an as small as possible scattering, consequently the transducer apparatus is, as a whole, well reproducible, the first temperature sensor 71 includes, according to an additional embodiment of the invention,—and as well as also shown schematically in FIG. 7, respectively 8 —, furthermore, a third coupling body 713 coupling its temperature detector 711 thermally with the fluid volume formed in the intermediate space. The third coupling body 713 contacts the fluid volume to form the third interface II13 of a first type. Coupling body 713 is composed, according to other embodiments of the invention, at least partially, especially namely predominantly or completely, of a material, of which a specific thermal conductivity $\lambda 723$ is greater than the specific thermal conductivity λF of the fluid FL2 in the intermediate space and/or greater than 0.1 W/(m·K), and of which a specific heat capacity cp713 is less than a specific heat capacity cpF of the fluid FL2 in the intermediate space and/or less than 2000 J/(kg·K). In advantageous manner, the material of the coupling body 713 is so selected matched to the fluid FL2 in the intermediate space that a ratio λ723/λF of the specific thermal conductivity λ723 of the material to the thermal conductivity λF of the fluid FL2 in the intermediate space is greater than 0.2, and/or that a ratio cp723/cpF of the specific heat capacity cp723 of the material to the heat capacity cpF of the fluid FL2 in the intermediate space is less than 1.5. The coupling body 713 can be formed —, for example, also completely—by means of a synthetic material, such as e.g. an epoxide resin or a silicone, applied on the temperature detector 711 of the temperature sensor 71, for example, also a synthetic material mixed with metal oxide particles. Alternatively or supplementally, the coupling body 713 can, in given cases, also be formed completely by means of a textile band or tape applied on the temperature detector 711, for example, a glass fiber textile band or tape, respectively also by means of sheet metal applied on the temperature detector 711, such as e.g. a sheet metal strip of stainless steel.

In an additional embodiment, moreover, also the temperature sensor 72—such as also shown schematically in FIG. 7, respectively 8—is formed by means of an additional, fourth coupling body 723, namely a fourth coupling body coupling its temperature detector 721 thermally with the fluid volume formed in the intermediate space. The fourth coupling body contacts the fluid volume formed in the intermediate space to form the fourth interface II14 of a first type. Coupling body 723 can in advantageous manner additionally be embodied to be of equal construction to that of the coupling body 713 of the temperature sensor 71. In accordance therewith, also the fourth coupling body 723 can at least partially—, for example, namely predominantly or completely—be produced of a material, of which a specific thermal conductivity λ723 is greater than the specific thermal conductivity λF and/or greater than 0.1 W/(m·K), and of which a specific heat capacity cp723 is less than the specific heat capacity cpF and/or less than 2000 J/(kg·K), for example, also in such a manner that a ratio λ723/λF of the specific thermal conductivity λ723 to the thermal conductivity λF is greater than 0.2 and/or a ratio cp723/cpF of the specific heat capacity cp723 to the heat capacity cpF is less than 1.5. Serving also for manufacture of the coupling body 723 can be, for example, a synthetic material applied on the temperature detector 721, in given cases, a synthetic material also useful for manufacture of the coupling body 713, respectively the coupling body 723 can also be formed by means of a section of a textile band or tape, respectively metal sheet, applied on the temperature detector 721, in given cases, such also useful for manufacture of the coupling body 713.

In order, on the one hand, to provide the temperature sensor 71 with as small as possible thermal inertia relative to changes of the tube temperature as a function of time, on the other hand, also, however, also to provide an as good as possible thermal coupling of the temperature sensor 71 to the wall of the tube also with an as compact as possible construction, the coupling body 712 is, according to an additional embodiment of the invention, at least partially —, for example, also predominantly or completely—produced of a material, for example, namely a thermally conductive adhesive, of which a specific thermal conductivity λ112 is greater than a specific thermal conductivity λF of the fluid FL2 in the intermediate space and/or greater than 1 W/(m·K). In advantageous manner, the material of the coupling body 712 is, in such case, furthermore, so selected that a ratio λ712/λF of the specific thermal conductivity λ712 of the material of the coupling body 712 to the specific thermal conductivity λF of the fluid FL2 in the intermediate space is greater than 2, and/or that a ratio cp712/cpF of a specific heat capacity cp712 of the material of the coupling body 712 to the heat capacity cpF of the fluid FL2 in the intermediate space is less than 1.5, especially in such a manner that the specific heat capacity cp712 is less than a specific heat capacity cpF of the fluid in the intermediate space. Moreover, also the coupling body 722 of the temperature sensor 72 can at least partially (or also completely) be produced of the same material as the coupling body 712 of the temperature sensor 71.

Figure 9:
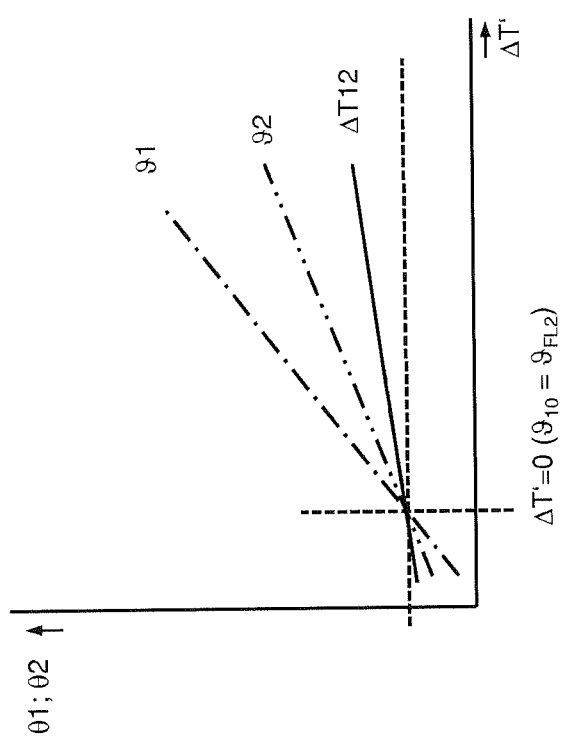
FIG. 9 is a graph of dependencies of measurement location temperatures (respectively therefrom derived temperature measurement signals) registered in a transducer apparatus of FIGS. 2, 3, respectively 7, 8, by means of their respective temperature sensors for a tube temperature and a tube ambient temperature, respectively a temperature difference existing therebetween.

Due, on the one hand, to the thermal coupling of the two temperature sensors 71, 72 to the wall of the tube, respectively, on the other hand, to the fluid volume surrounding such—with or without coupling body 713, respectively 714 —, each of the measurement location temperatures $\vartheta_1$, $\vartheta_2$ is determined, on the one hand, by a temperature difference $\Delta T'$ ($\Delta T' = \vartheta_{10} - \vartheta_{FL2}$) existing between the tube temperature $\vartheta_{10}$ and the tube ambient temperature $\vartheta_{FL2}$, respectively a temperature difference $\Delta T''$ ($\Delta T'' = \vartheta_{FL1} - \vartheta_{FL2}$) existing between the measured fluid temperature $\vartheta_{FL1}$ and the tube ambient temperature $\vartheta_{L2}$ and, on the other hand, however, also, in each case, by the actual values of the above discussed thermal resistances R1, R2, R3 and R4, respectively resistance ratios resulting therefrom. With the assumption made for the calculation model underlying the equivalent circuit diagram illustrated in FIG. 6 that the heat flux Q3 traversing the thermal resistance R3 corresponds to the heat flux Q1 traversing the thermal resistance R1, respectively the heat flux Q4 traversing the thermal resistance R4 corresponds to the heat flux Q2 traversing the thermal resistance R2, i.e. Q3=Q1, respectively Q4=Q2, it can, first of all, be derived that the measurement location temperature $\vartheta_1$, respectively the measurement location temperature $\vartheta_2$ approximately, respectively at essentially stationary temperature distribution within the transducer apparatus, fulfill, among others, one of the conditions:

$$\vartheta_1 = (\vartheta_{FL2} - \vartheta_{10}) \cdot \frac{R1}{R1 + R3} + \vartheta_{10} \sim -(\vartheta_{FL1} - \vartheta_{FL2}) \cdot \frac{R1}{R1 + R3} + \vartheta_{10} \quad (1)$$

$$\vartheta_2 = (\vartheta_{FL2} - \vartheta_{10}) \cdot \frac{R2}{R2 + R4} + \vartheta_{10} \sim -(\vartheta_{FL1} - \vartheta_{FL2}) \cdot \frac{R2}{R2 + R4} + \vartheta_{10} \quad (2)$$

$$\vartheta_1 = (\vartheta_{10} - \vartheta_{FL2}) \cdot \frac{R3}{R1 + R3} + \vartheta_{FL2} \sim (\vartheta_{FL1} - \vartheta_{FL2}) \cdot \frac{R3}{R1 + R3} + \vartheta_{FL2} \quad (3)$$

$$\vartheta_2 = (\vartheta_{10} - \vartheta_{FL2}) \cdot \frac{R4}{R2 + R4} + \vartheta_{FL2} \sim (\vartheta_{FL1} - \vartheta_{FL2}) \cdot \frac{R4}{R2 + R4} + \vartheta_{FL2} \quad (4)$$

respectively that the measurement location temperatures 41, 42 in the case of these conditions depend on the tube ambient temperature $\vartheta_{FL2}$ as well as the measured fluid temperature $\vartheta_{FL1}$, respectively the tube temperature $\vartheta_{10}$. Furthermore, there results, additionally, that also a measurement location temperature difference $\Delta T12 = \vartheta_1 - \vartheta_2$ corresponding to a difference between the two measurement location temperatures $\vartheta_1$, $\vartheta_2$ represented by the temperature measurement signals θ1, θ2 is at least approximately proportional to the above indicated temperature difference $\Delta T'$ between the tube temperature $\vartheta_{10}$ and the tube ambient temperature $\vartheta_{FL2}$ according to the following relationship illustrated graphically in FIG. 9:

$$\vartheta1 - \vartheta2 = (\vartheta_{10} - \vartheta_{FL2}) \cdot \left( \frac{R1}{R1+R3} - \frac{R2}{R2+R4} \right) \quad (5)$$

respectively that, conversely, the tube temperature $\vartheta_{10}$ is determinable from the two measurement location temperatures $\vartheta1$, $\vartheta2$ according to the relationship:

$$\vartheta_{10} = \frac{1+\frac{R3}{R1}}{\frac{R3}{R1}-\frac{R4}{R2}} \cdot \vartheta1 - \frac{1+\frac{R4}{R2}}{\frac{R3}{R1}-\frac{R4}{R2}} \cdot \vartheta2 \quad (6)$$

With knowledge of the thermal resistances R1, R2, R3, R4, respectively the corresponding thermal resistance ratios R1/R3, R4/R2, thus, e.g. the temperature difference ΔT', respectively also the tube temperature $\vartheta_{10}$, can be calculated directly based on the two measurement location temperatures $\vartheta1$, $\vartheta2$, respectively their measurement location temperature difference ΔT12.

Each of the above indicated thermal resistances R1, R2, R3 and R4 is—such as already mentioned —, in each case, decisively, respectively completely, defined by material properties, such as e.g. a specific thermal conductivity λ, as well as dimensions of the respective coupling body, respectively the wall of the tube, such as e.g. a respective effective length $L_{th}$ of the respective coupling body for the respectively traversing heat flux as well as a surface area $A_{th}$ of a respective effective cross sectional area of the respective coupling body for the heat flux, for example, namely the surface areas of the respective interfaces II21, II22, and/or by corresponding material properties of the wall of the tube 10, respectively of the fluid FL2 in the intermediate space 100', consequently already alone by earlier, at least approximately known, parameters, equally as well parameters essentially unchangeable over a longer operational time frame parameter. Thus, each of the thermal resistances R1, R2, R3, R4 can be earlier sufficiently exactly determined by means of the mentioned parameters (λ, $A_{th}$, $L_{th}$), for example, by experimental measurements and/or by calculations. For example, based on the known relationship:

$$Rth = \frac{L_{eff}}{\lambda \cdot A_{eff}} \quad (7)$$

a heat conduction resistance co-determining the thermal resistance R1, respectively R2—namely a heat conduction resistance representing a temperature reduction related to a heat flux due to heat conduction processes—can be quantified, for example, namely calculated in units of K/W (Kelvin per Watt). With knowledge of the material properties of the materials respectively actually used for manufacture of the temperature sensors as well as the actual shape and dimensions of the previously indicated, interfaces II13, II14, II21, II22 formed by means of the temperature sensors, also the resistance values for the previously indicated heat transfer resistances respectively co-determining the thermal resistances R1, R2, R3, R4 can be sufficiently exactly established, respectively sufficiently exactly earlier ascertained. Alternatively or supplementally, the thermal resistances R1, R2, R3, R4, respectively the corresponding to thermal resistance ratios R1/R3, R4/R2, can, for example, also be ascertained experimentally by means of calibration measurements performed on the respective transducer apparatus.

Figure 10:
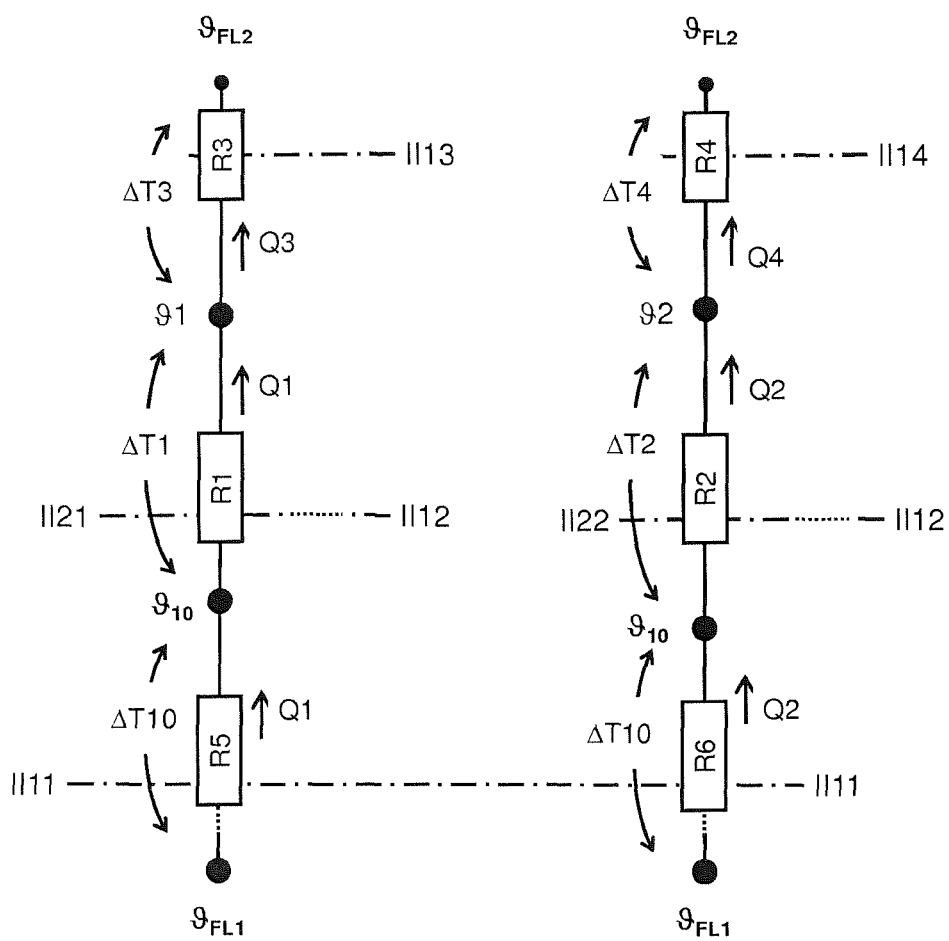
FIG. 10 shows a resistor network formed by means of a plurality of discrete thermal resistances in the manner of an equivalent circuit and serving for explaining heat fluxes, respectively corresponding temperature drops, in a transducer apparatus of FIGS. 2, 3, respectively 7, 8, including the tube.

Further taking into consideration also additional thermal resistances provided by the wall of the tube 10 and provoking a temperature difference ΔT10 between the interface II11 of first type and the interface II12 of first type, namely —, as well as also illustrated in FIG. 10 based on an equivalent circuit diagram correspondingly supplemented in comparison to that in FIG. 6—a fifth thermal resistance R5 (R5=ΔT10/Q1) opposing the heat flux Q1 also flowing within the wall of the tube between the interface II11 of first type and the interface II12 of first type as well as a sixth thermal resistance R6 (R6=ΔT10/Q2) opposing the heat flux Q2 also flowing within the wall of the tube between the interface II11 of first type and the interface II12 of first type, additionally also a dependence of the measurement location temperature difference ΔT12 on the temperature difference ΔT"(ΔT"=$\vartheta_{FL1}$−$\vartheta_{FL2}$) existing between the measured fluid temperature $\vartheta_{FL1}$ and the tube ambient temperature $\vartheta_{FL2}$, respectively, conversely, also a dependence of the measurement location temperature difference ΔT12 on the temperature difference ΔT"(ΔT"=$\vartheta_{FL1}$−$\vartheta_{FL2}$) existing between the measured fluid temperature $\vartheta_{FL1}$ and the tube ambient temperature $\vartheta_{FL2}$ can be formulated, respectively, in each case, expressed as a corresponding formula:

$$\vartheta1 - \vartheta2 = (\vartheta_{FL1} - \vartheta_{FL2}) \cdot \left( \frac{R3}{R1+R3+R5} - \frac{R4}{R2+R4+R6} \right) \quad (8)$$

respectively $$\vartheta_{FL1} = \frac{1+\frac{R3}{R1+R5}}{\frac{R3}{R1+R5}-\frac{R4}{R2+R6}} \cdot \vartheta1 - \frac{1+\frac{R4}{R2+R6}}{\frac{R3}{R1+R5}-\frac{R4}{R2+R6}} \cdot \vartheta2. \quad (9)$$

Also the above mentioned thermal resistances R5, respectively R6, created by the wall of the tube can be basically earlier sufficiently exactly quantified, namely calculated based on material properties of the tube, such as, for instance, its specific thermal conductivity λ10, respectively specific heat capacitance cp10, as well as its dimensions, especially its wall thickness s, for example, according to one of the formulas derived from the above indicated Equation (7) corresponding to the equivalent circuit diagram shown in FIG. 10:

$$R5 = \frac{\Delta T10}{Q1} \approx \frac{L_{eff}}{\lambda10 \cdot A_{eff}} \quad (10)$$

$$R6 = \frac{\Delta T10}{Q2} \approx \frac{L_{eff}}{\lambda10 \cdot A_{eff}}. \quad (11)$$

Investigations have, in such case, furthermore, shown that, in the case of using the wall thickness s as effective length $L_{eff}$ (s→Len'), a resistance value then ascertained based on twice the area of the respectively associated interface II21, respectively II22, consequently based on two times the area $A_{th}$ (2·$A_{th}$→$A_{eff}$) of the cross sectional area of the respectively associated coupling body 712, 722 respectively effective for the respective heat flux Q1, Q2, a very exact estimation for the heat conduction fraction of the thermal resistance R5 effective for the heat flux Q1, respectively of the thermal resistance R6 effective for the heat flux Q2, is, consequently, as a whole, a good approximation for the respective thermal resistance R5, respectively R6.

Since basically each of the above indicated thermal resistances R1, R2, R3, R4, R5, R6, respectively each of the resistance ratios derived therefrom, is earlier determinable, namely quantifiable, then, based on the measurement location temperatures $\vartheta 1$, $\vartheta 2$ registered by means of the temperature sensors 71, 72, respectively the temperature measurement signals θ1, θ2 respectively representing these temperatures, accordingly also the tube temperature 410 can be calculated, respectively measured,—, for example, by applying Equation (6)—and/or the measured fluid temperature $\vartheta_{FL1}$—, for example, namely by applying Equation 9.

The measuring and operating electronics ME is, consequently, according to an additional embodiment of the invention, furthermore, also adapted, using both the first temperature measurement signal θ1 as well as also the second temperature measurement signal θ2, to generate at least one target temperature measured value $X_\Theta$, namely a measured value representing the particular target temperature, for example, namely the tube temperature or the measured fluid temperature; this, for example, in such a manner that the measuring and operating electronics ME, first of all based on the temperature measurement signal θ1, ascertains a first measurement location temperature measured value $X_1$ representing the measurement location temperature 41 and based on the temperature measurement signal θ2 ascertains a second measurement location temperature measured value $X_2$ representing the measurement location temperature $\vartheta 2$ and thereafter calculates the target temperature measured value $X_\Theta$ using both the measurement location temperature measured value $X_1$ as well as also the measurement location temperature measured value $X_2$. The calculating of the target temperature measured value $X_\Theta$ can occur e.g. using a formula dependent on the measurement location temperature measured values $X_1$, $X_2$ as well as earlier ascertained numerical constants α, β stored in the measuring and operating electronics ME, respectively by using a corresponding formula:

$$X_\Theta = \alpha \cdot X_{\theta 1} + \beta \cdot X_{\theta 2} \tag{12}$$

and represents, consequently, a temperature at an apparatus reference point (poi) established by the size of the constants α, β, respectively a size ratio α/β derived therefrom. In the case of application of only two measurement location temperature measured values ascertained based on the temperature measurement signals, the constants α, β contained in above referenced formula are in advantageous manner so selected that they fulfill the condition α+β=1. The constants α, β can, in such case, be so defined that the thereby ultimately set apparatus reference point is removed both from the first temperature sensor 71 as well as also from the second temperature sensor 72, especially namely is located within the tube; this, for example, also such that the target temperature represented by the target temperature measured value corresponds to the measured fluid temperature $\vartheta_{FL1}$ or also the tube temperature $\vartheta_{10}$. The tube temperature $\vartheta_{10}$ is not least of all for the above-described case, in which the transducer apparatus MT is embodied as a measuring transducer of vibration-type, of special interest, since, among others, a modulus of elasticity of the respective material the wall of the tube, as well as also spatial dimensions of the tube, consequently the oscillation characteristics of the respective tube defined thereby, are mentionably also dependent on the tube temperature $\vartheta_{10}$. For example,—with application of Eq. (6)—, the apparatus reference point can be positioned at the interface II21 of second type, consequently (virtually), respectively in, the wall of the tube 10, respectively the measuring and operating electronics ME can be correspondingly adapted to ascertain, respectively to output, the target temperature measured value $X_\Theta$ as measured value for the tube temperature $\vartheta_{10}$ in that the constants α, β are so selected that the condition:

$$\alpha = \frac{1 + \frac{R3}{R1}}{\frac{R3}{R1} - \frac{R4}{R2}} \tag{13}$$

as well as the condition:

$$\beta = -\frac{1 + \frac{R4}{R2}}{\frac{R3}{R1} - \frac{R4}{R2}} \tag{14}$$

and/or the condition:

$$\beta = 1 - \alpha \tag{15}$$

are fulfilled. Alternatively or supplementally,—namely by applying Eq. (9)—the apparatus reference point can, however, also be positioned at the interface II11 of a first type, consequently (virtually) within the lumen 10' of the tube 10, respectively within the fluid FL1 guided therein, respectively the measuring and operating electronics ME can be correspondingly adapted to ascertain, respectively to output, the target temperature measured value $X_\Theta$ as measured value for the measured fluid temperature $\vartheta_{FL1}$. This can be implemented in a simple manner, taking into consideration also the thermal resistances R5 and R6 caused by the wall of the tube, by selecting the constants α, β such that they fulfill the condition:

$$\alpha = \frac{1 + \frac{R3}{R1 + R5}}{\frac{R3}{R1 + R5} - \frac{R4}{R2 + R6}} \tag{16}$$

as well as the condition:

$$\beta = -\frac{1 + \frac{R4}{R2 + R6}}{\frac{R3}{R1 + R5} - \frac{R4}{R2 + R6}} \tag{17}$$

Resulting from the combination of the equivalent circuit diagram illustrated in FIG. 6 and the Equations (5), respectively (6), it is, furthermore, the case that, in order actually to be able to represent the tube temperature $\vartheta_{10}$ as a function of temperature differences ΔT1, ΔT2, respectively the measurement location temperatures $\vartheta 1$, $\vartheta 2$, the thermal resistances R1, R2, R3 and R4 must basically be so dimensioned that the thereby provoked temperature differences ΔT1, ΔT2, respectively measurement location temperatures $\vartheta 1$, $\vartheta 2$, differ from one another, consequently the measurement location temperature difference ΔT12 derived therefrom is, as a result, mentionably different from zero, respectively the following relationships hold, respectively must hold, for the temperature differences ΔT1, ΔT2:

$$\frac{\Delta T1}{\Delta T2} = \frac{\vartheta_1 - \vartheta_{10}}{\vartheta_2 - \vartheta_{10}} = \frac{R1}{R1+R3} \cdot \frac{R2+R4}{R2} = \frac{1+\frac{R4}{R2}}{1+\frac{R3}{R1}} \overset{!}{\neq} 1$$

Taking this into consideration and applying the above Equations (1) and (2), in the case of the transducer apparatus of the invention, the thermal resistances R1, R2, R3, R4 are, consequently, furthermore, so dimensioned that they fulfill the condition:

$$\frac{1+\frac{R4}{R2}}{1+\frac{R3}{R1}} < 1 \tag{18}$$

In order, in such case, also to be able to cancel possible measuring inaccuracies of the temperature detectors of both temperature sensors, respectively measurement uncertainties, respectively confidence intervals, caused by manufacturing tolerances, for instance, in such a manner that a temperature difference ΔT' having a positive sign always is represented by an equally positive instantaneous measurement location temperature difference ΔT12, the above discussed thermal resistances R1, R2, R3, R4 are, furthermore, so dimensioned according to an additional embodiment that, as a result, also the condition:

$$\frac{1+\frac{R4}{R2}}{1+\frac{R3}{R1}} < 0.9 \tag{19}$$

is fulfilled. In order additionally also to be able to assure that the assumption underpinning the relationship formulated with equation (5), that each of the two measurement location temperatures ϑ1, ϑ2 is, in each case, equally dependent on the temperature difference ΔT', is actually true, consequently that, during operation of the transducer apparatus, the following holds for the temperature differences ΔT1, ΔT2, ΔT3, ΔT4 as exactly as possible:

$$\Delta T1 + \Delta T3 = \Delta T2 + \Delta T4 = \Delta T' \tag{20}$$

the thermal resistances R1, R2, R3, R4 in the case of the transducer apparatus of the invention are, furthermore, also so dimensioned that they, as a whole, additionally also fulfill a condition:

$$\frac{1+\frac{R4}{R2}}{1+\frac{R3}{R1}} > 0.005, \tag{21}$$

especially namely also a condition:

$$\frac{1+\frac{R4}{R2}}{1+\frac{R3}{R1}} > 0.01 \tag{22}$$

In this regard, in the case of applying typical, respectively also above indicated, materials for manufacture of the temperature sensors, respectively in the case of embodiment of the temperature sensors in typical structures, it can most often directly be achieved that a spatial separation between the two temperature sensors 71, 72, not least of all also between the interfaces II13, II14 of a first type respectively formed therewith, is embodied small enough, in order that the interfaces during operation of the transducer apparatus are positioned within a zone of the fluid volume having no or, at most, negligible, temperature gradients, and, are supplied consequently essentially with the same ambient temperature. For the very simply implemented case, in which the two thermal resistances R3, R4 are embodied equally, consequently the condition:

$$R3 = R4 \tag{23}$$

is fulfilled, the measurement specifications formulated with the Equations (18), respectively (21), can be fulfilled in very simple, equally as a well effective, manner by a corresponding dimensioning alone of the thermal resistances R1, R2, consequently—assuming equally constructed temperature detectors 711, 721—Equations (18), respectively (21), can be followed alone by a correspondingly adapted embodying of the two coupling bodies 712, 722.

The invention claimed is:

1. A transducer apparatus, comprising:
    a transducer housing exhibiting a cavity encased by a wall;
    a tube exhibiting a lumen surrounded by a wall, said tube is arranged within the cavity of said transducer housing in such a manner that between an inner surface of the wall of said transducer housing facing the cavity and an outer surface of the wall of said tube facing the cavity an intermediate space is formed, and
    said tube is adapted to guide in its lumen a fluid, in such a manner that said inner surface of the wall of said tube facing the lumen is contacted by the fluid guided in the lumen in order to form a first interface of a first type, wherein the first interface of the first type is an interface between the fluid guided in the lumen of the tube and the wall of said tube;
    a first temperature sensor including a first temperature detector arranged within said intermediate space and a first coupling body coupling said first temperature detector thermally conductively with the wall of said tube, said first temperature sensor being adapted to register a first measurement location temperature, wherein a temperature at a first temperature measurement location is formed by means of said first temperature detector, and to transduce said first measurement location temperature into a first temperature measurement signal, said first temperature measurement signal is a first electrical measurement signal representing the first measurement location temperature;
    a second temperature sensor including a second temperature detector spaced from said first temperature detector and arranged within said intermediate space and a second coupling body coupling said second temperature detector thermally conductively with the wall of said tube, said second temperature sensor being adapted to register a second measurement location temperature, wherein a temperature at a second temperature measurement location is formed by means of said second temperature detector, and to transduce said second measurement location temperature into a second temperature measurement signal, said second temperature measurement signal is a second electrical measurement signal representing the second measurement location temperature; wherein:

said transducer housing and said tube are adapted to hold a fluid in said intermediate space in order to form a fluid volume surrounding said tube, in such a manner that said outer surface of the wall of said tube facing said intermediate space is contacted by the fluid held in said intermediate space in order to form a second interface of the first type, wherein the second interface of the first type is an interface between the fluid held in said intermediate space and the wall of said tube;

said first temperature sensor contacts by means of said first coupling body the outer surface of the wall of said tube forming a first interface of a second type, wherein the first interface of the second type is an interface between the first coupling body and the wall of said tube and said second temperature sensor contacts by means of said second coupling body the outer surface of the wall of said tube forming a second interface of the second type, wherein the second interface of the second type is an interface between the second coupling body and the wall of said tube, in such a manner that:

a first thermal resistance, R1, opposes a first heat flux, resulting from a temperature difference between said first interface of the second type and said first temperature measurement location, totally passing through the first interface of the second type and flowing further to the first temperature measurement location;

a second thermal resistance, R2, opposes a second heat flux, resulting from a temperature difference between said second interface of the second type and the second temperature measurement location, totally passing through the second interface of the second type and flowing further to the second temperature measurement location; and the fluid volume surrounding said tube contacts said first temperature sensor to form a third interface of the first type as well as contacts said second temperature sensor to form a fourth interface of the first type, in such a manner that:

a third thermal resistance, R3, opposes a third heat flux, resulting from a temperature difference between said third interface of the first type and the first temperature measurement location, flowing from the first temperature measurement location totally to said third interface of the first type, equally as well totally passing through said third interface of the first type; and a fourth thermal resistance, R4, opposes a fourth heat flux, resulting from a temperature difference between said fourth interface of the first type and the second temperature measurement location, flowing from the second temperature measurement location totally to said fourth interface of the first type, equally as well totally passing through said fourth interface of the first type; and said first thermal resistance, R1, said second thermal resistance, R2, said third thermal resistance, R3, as well as said fourth thermal resistance, R4, are so dimensioned that a condition $$0.005 < \frac{1+\frac{R4}{R2}}{1+\frac{R3}{R1}} < 1$$

is fulfilled.

2. The transducer apparatus as claimed in claim 1, wherein:
said first thermal resistance, R1, is less than 1000 K/W; and
said second thermal resistance, R2, is less than 1000 K/W.

3. The transducer apparatus as claimed in claim 1, wherein:
said first thermal resistance, R1, is less than 30 K/W.

4. The transducer apparatus as claimed in claim 1, wherein:
said third thermal resistance, R3, and said fourth thermal resistance, R4, fulfill a condition R3=R4.

5. The transducer apparatus as claimed in claim 1, wherein:
said first thermal resistance, R1, said second thermal resistance, R2, said third thermal resistance, R3, as well as said fourth thermal resistance, R4 fulfill a condition $$\frac{1+\frac{R4}{R2}}{1+\frac{R3}{R1}} < 0.9;$$

and/or
wherein said first thermal resistance, R1, said second thermal resistance, R2, said third thermal resistance, R3, as well as said fourth thermal resistance, R4, fulfill a condition $$\frac{1+\frac{R4}{R2}}{1+\frac{R3}{R1}} > 0.01.$$

6. The transducer apparatus as claimed in claim 1, wherein:
said first coupling body is composed at least partially of a material of which a specific thermal conductivity is greater than a specific thermal conductivity of the fluid in the intermediate space and/or greater than 1 W/(m·K), and of which a specific heat capacity is less than a specific heat capacity of the fluid in the intermediate space and/or less than 2000 J/(kg·K).

7. The transducer apparatus according to claim 6, wherein:
said second coupling body is composed at least partially of a material of which material a specific thermal conductivity is greater than the specific thermal conductivity of the material of said first coupling body and/or greater than 10 W/(m·K), and/or of which material a specific heat capacity is less than the specific heat capacity of the material of said first coupling body and/or less than 1000 J/(kg·K).

8. The transducer apparatus as claimed in claim 1, wherein:
said third thermal resistance, R3, is greater than 500 K/W, and/or less than 20000 K/W; and/or said fourth thermal resistance, R4, is greater than 500 K/W, and/or less than 20000 K/W.

9. The transducer apparatus as claimed in claim 1, wherein:
said first temperature sensor includes a third coupling body coupling said first temperature detector thermally with the fluid volume surrounding the tube and contacting the fluid volume surrounding the tube to form said third interface of the first type.

10. The transducer apparatus as claimed in claim 9, wherein:
said second temperature sensor includes a fourth coupling body coupling said second temperature detector thermally with the fluid volume surrounding the tube and contacting the fluid volume surrounding the tube to form said fourth interface of the first type.

11. The transducer apparatus as claimed in claim 10, wherein:
said third and fourth coupling bodies are constructed equally to one another.

12. The transducer apparatus according to claim 10, wherein:
said fourth coupling body is composed at least partially of a material of which a specific thermal conductivity is greater than a specific thermal conductivity of the fluid in the intermediate space and/or greater than 0.1 W/(m·K), and of which a specific heat capacity is less than a specific heat capacity of the fluid in the intermediate space and/or less than 2000 J/(kg·K).

13. The transducer apparatus as claimed in claim 10, wherein:
said fourth coupling body is formed by means of a synthetic material applied on the second temperature detector.

14. The transducer apparatus as claimed in claim 10, wherein:
said fourth coupling body is formed by means of a textile band or tape applied on said second temperature detector.

15. The transducer apparatus as claimed in claim 10, wherein:
said fourth coupling body is formed by means of sheet metal applied on said second temperature detector.

16. The transducer apparatus as claimed in claim 9, wherein:
said third coupling body is formed by means of a synthetic material applied on said first temperature detector.

17. The transducer apparatus as claimed in claim 9, wherein:
said third coupling body is formed by means of a textile band or tape applied on said first temperature detector.

18. The transducer apparatus as claimed in claim 9, wherein:
said third coupling body is formed by means of sheet metal applied on said first temperature detector.

19. The transducer apparatus as claimed in claim 9, wherein:
said third coupling body is composed at least partially of a material of which a specific thermal conductivity is greater than a specific thermal conductivity of the fluid in the intermediate space and/or greater than 0.1 W/(m·K), and of which a specific heat capacity is less than a specific heat capacity of the fluid in the intermediate space and/or less than 2000 J/(kg·K).

20. The transducer apparatus as claimed in claim 1, wherein:
said first coupling body shows a heat capacity, C1, which is less than 200 J/K; and
said second coupling body shows a heat capacity, C2, which is less than 200 J/K, wherein $$\frac{1}{10} < \frac{C1}{C2} < 1.$$

21. The transducer apparatus as claimed in claim 20, wherein:
said heat capacity, C1, of said first coupling body and said second heat capacity, C2, of said second coupling body fulfill a condition $$\frac{1}{1000} < \frac{C1}{C2} < 1.$$

22. The transducer apparatus as claimed in claim 1, wherein:
the wall of the tube has a wall thickness which is greater than 0.5 mm and/or less than 10 mm; and/or
said tube has an inner diameter which is greater than 0.5 mm and/or less than 200 mm; and/or
said tube is so dimensioned that it has an inner diameter to wall thickness ratio, defined as a ratio of an inner diameter of said tube to a wall thickness of the wall of said tube, which is less than 25:1 and/or greater than 5:1.

23. The transducer apparatus as claimed in claim 1, wherein:
said first temperature sensor is connected with the outer surface of the wall of said tube to form said first coupling body by the bonding of materials.

24. The transducer apparatus as claimed in claim 1, wherein:
said first coupling body is formed by means of a synthetic material located between the wall of said tube and said first temperature detector.

25. The transducer apparatus as claimed in claim 24, wherein:
the synthetic material is a silicone rubber.

26. The transducer apparatus as claimed in claim 1, wherein:
said second coupling body is formed by means of a disk located between the wall of said tube and said second temperature detector and composed of a metal.

27. The transducer apparatus as claimed in claim 26, wherein:
said disk has a passageway having an inner surface facing the outer surface of the wall of said tube.

28. The transducer apparatus as claimed in claim 1, wherein:
said first temperature sensor and said second temperature sensor are spaced azimuthally from one another with reference to an imaginary longitudinal axis of said tube; and/or
said first temperature sensor and said second temperature sensor, are spaced axially with reference to the imaginary longitudinal axis of said tube.

29. The transducer apparatus as claimed in claim 1, wherein:
said tube is further adapted to be flowed through by the fluid and during that to be caused to vibrate.

30. The transducer apparatus as claimed in claim 1, further comprising:
an oscillation exciter for exciting and maintaining mechanical oscillations of the said tube about an associated static resting position; as well as an oscillation sensor for registering mechanical oscillations of said tube.

31. A measuring system for measuring at least one measured variable of a flowing fluid, which measuring system comprises:
for the guiding of the fluid, a transducer apparatus as claimed in claim 1; and
a measuring and operating electronics.

32. The measuring system as claimed in claim 31, wherein:
an oscillation sensor is adapted to deliver an oscillatory signal representing oscillations of said tube; and
said measuring and operating electronics is adapted, using both the first temperature measurement signal as well as also the second temperature measurement signal, as well as the oscillation signal, to generate a density measured value.

33. The measuring system as claimed in claim 31, wherein:
said measuring and operating electronics is adapted, using both the first temperature measurement signal generated by means of said transducer apparatus as well as also the second temperature measurement signal generated by means of the transducer apparatus, to generate a measured value, which represents the at least one measured variable.

34. The measuring system as claimed in claim 31, wherein:
said measuring and operating electronics is adapted, using both the first temperature measurement signal as well as also the second temperature measurement signal, to generate at least one temperature measured value representing a target temperature, which target temperature is a temperature at an apparatus reference point predetermined for the measuring system and fixed within said transducer apparatus.

35. The measuring system as claimed in claim 34, wherein:
the apparatus reference point is located within said transducer apparatus.

\* \* \* \* \*